(12) United States Patent
Inoue

(10) Patent No.: US 9,724,185 B2
(45) Date of Patent: Aug. 8, 2017

(54) RETRIEVABLE FILTER

(71) Applicant: PTMC Institute, Kyoto-shi, Kyoto (JP)

(72) Inventor: Kanji Inoue, Kyoto (JP)

(73) Assignee: PTMC Institute, Kyoto-shi, Kyoto (JP)

( * ) Notice: Subject to any disclaimer, the term of this patent is extended or adjusted under 35 U.S.C. 154(b) by 146 days.

(21) Appl. No.: 14/583,519

(22) Filed: Dec. 26, 2014

(65) Prior Publication Data

US 2016/0008121 A1 Jan. 14, 2016

(30) Foreign Application Priority Data

Jul. 10, 2014 (JP) .................................. 2014-141881

(51) Int. Cl.
*A61F 2/01* (2006.01)
*A61F 2/958* (2013.01)
(Continued)

(52) U.S. Cl.
CPC ................. *A61F 2/013* (2013.01); *A61F 2/82* (2013.01); *A61F 2/958* (2013.01); *A61F 2/962* (2013.01);
(Continued)

(58) Field of Classification Search
CPC .... A61F 2/013; A61F 2/82; A61F 2/92; A61F 2/958; A61F 2/962; A61F 2002/011;
(Continued)

(56) References Cited

U.S. PATENT DOCUMENTS

| 6,443,971 B1* | 9/2002 | Boylan | A61F 2/013 606/200 |
| 2002/0128678 A1* | 9/2002 | Petersen | A61F 2/013 606/200 |

(Continued)

FOREIGN PATENT DOCUMENTS

| WO | 02054984 A2 | 7/2002 |
| WO | 02069844 A2 | 9/2002 |

(Continued)

OTHER PUBLICATIONS

European Patent Office, Extended European Search Report Issued in Application No. 14199965.6, Nov. 11, 2015, 8 pages.
(Continued)

*Primary Examiner* — Melanie Tyson
*Assistant Examiner* — Rachel S Highland
(74) *Attorney, Agent, or Firm* — Alleman Hall Creasman & Tuttle LLP

(57) ABSTRACT

To provide a medical tool that dramatically simplifies operations and has a small number of parts. For this purpose, the medical tool includes: an outer tube; a core that is inserted into the outer tube so as to be movable forward and backward; a medical tool main body that is attached to the core; and a containing member that is attached to the fore end of the outer tube, and is configured such that when by moving the outer tube forward relatively to the core, the containing member is made to approach the medical tool main body released out of the containing member, the
(Continued)

containing member makes driving force for operating the medical tool main body act on the medical tool main body.

11 Claims, 32 Drawing Sheets

(51) Int. Cl.
   *A61F 2/962* (2013.01)
   *A61F 2/82* (2013.01)

(52) U.S. Cl.
   CPC . *A61F 2002/011* (2013.01); *A61F 2230/0067* (2013.01)

(58) Field of Classification Search
   CPC .............. A61F 2/95; A61F 2002/9528; A61F 2002/9534; A61F 2/01
   See application file for complete search history.

(56) References Cited

U.S. PATENT DOCUMENTS

| | | | |
|---|---|---|---|
| 2003/0093106 A1* | 5/2003 | Brady | A61F 2/013 606/194 |
| 2003/0187474 A1* | 10/2003 | Keegan | A61F 2/0095 606/200 |
| 2004/0243173 A1 | 12/2004 | Inoue | |
| 2005/0096663 A1* | 5/2005 | Sater | A61M 25/0105 606/108 |
| 2005/0159774 A1* | 7/2005 | Belef | A61F 2/013 606/200 |
| 2006/0173475 A1* | 8/2006 | Lafontaine | A61B 17/32075 606/159 |
| 2010/0228281 A1* | 9/2010 | Gilson | A61F 2/01 606/200 |

FOREIGN PATENT DOCUMENTS

| | | |
|---|---|---|
| WO | 03030740 A1 | 4/2003 |
| WO | 2011144240 A1 | 11/2011 |

OTHER PUBLICATIONS

Japan Patent Office, Office Action Issued in Patent Application No. 2013-070273, Oct. 18, 2016, 3 pages.

\* cited by examiner

RETRIEVABLE FILTER

TECHNICAL FIELD

The present invention relates to a medical tool that is inserted into the body with use of a catheter to provide treatment, such as an intravascular free piece capturing tool adapted to capture an atheroma or a thrombus that was detached when indwelling a stent or the like in a stenosis site in a blood vessel.

BACKGROUND ART

As this sort of medical tool, for example, there is an intravascular free piece capturing tool developed by the present inventor (see Patent Literature 1). The free piece capturing tool is one in which a bag-like filter member having an opening is attached to the tip part of a wire, and by placing the filter member on the downstream side of a surgical operation site in a blood vessel (e.g., a stenosis site in a blood vessel to be dilated by a balloon stent), can capture a thrombus detached by a surgical operation to prevent secondary occlusion of the blood vessel by the detached thrombus.

The filter member described in Patent Literature 1 is formed of a bag-like filter having an opening and an elastic ring for shaping the opening, and the elastic ring is supported by multiple supporting wire members radially extending from the wire. At the beginning, the filter member is contained in a containing member integrally attached to the fore end of a conveying tube with the elastic ring and the filter being folded and elongated. At this time, the wire is also inserted into the conveying tube.

To place such a filter member in a target site, i.e., on the slightly downstream side of the stenosis site, by inserting the containing member containing the filter member into a main catheter preliminarily inserted into the blood vessel, and sending out the conveying tube and the wire together, the filter member is conveyed to the target site.

Then, by without moving the wire, drawing only the conveying tube toward the operating end to move only the containing member backward, the filter member is released out of the containing member. In doing so, the filter member naturally opens the opening by restoring force of the elastic ring, and thereby the filter member is arranged in the blood vessel in an attitude capable of capturing the free piece.

After arranging the filter member in this manner, only the conveying tube is pulled closer, and withdrawn together with the containing member.

Subsequently, along the wire connected to the filter member, a balloon catheter or a stent is sent to the stenosis site to treat the stenosis site.

On the other hand, after withdrawing the balloon catheter after the treatment, it is necessary to withdraw the filter member.

For this purpose, a withdrawing tube different from the conveying tube is sent out from the operating end along the wire. In doing so, the withdrawing tube pushes a small-diameter tube called slider, which is preliminarily arranged on the slightly near to the operating end side of the filter member, and slides the small-diameter tube toward the supporting wire members. This makes the supporting wire members be gradually drawn into the slider, and thereby contractile force toward the center of the elastic ring acts on the elastic ring. The contractile force folds the elastic ring upward and downward in four at positions preliminarily given a tendency, and thereby the elastic ring is formed in an elongated shape to close the opening of the filter.

As described, the withdrawing tube also acts as an actuator to provide external force for closing the opening of the filter member. Subsequently, in that state, the guide wire and the withdrawing tube is pulled closer to withdraw the filter member through the catheter.

CITATION LIST

Patent Literature

Patent Literature 1: Re-publication of PCT International Publication No. 03-30740

SUMMARY OF INVENTION

Technical Problem

However, with such a configuration as described above, to perform conveyance and withdrawing operations of the filter member, it is necessary to send/draw the different dedicated tubes each time, and therefore the operations are complicated and require time.

For example, when placing the filter member, filter member is released out of the containing member and placed in the target site, and then only the conveying tube covering the wire should be pulled back a rather long distance while holding the wire without moving the wire. Similarly, at the time of withdrawing the filter member, the withdrawing tube should be sent out without moving the wire. Such operations are required for other types of intravascular free piece capturing tool that has different structure but uses a bag-like filter, as well.

Such problems are common to any medical tool main body that is contained in a containing member provided at the fore end of a tube and inserted into the body, then released out of the containing member in a target site by operating the tube, and after that, operated by pulling back the tube, inserting another tube, and giving driving force.

Therefore, the present invention is made in order to solve the above-described problems at once, and a main intended object thereof is to provide a medical tool that dramatically simplifies operations and has a small number of parts.

Solution to Problem

That is, the medical tool according to the present invention is one that includes: an outer tube that is inserted into a body; a core that is inserted into the outer tube so as to be movable forward and backward; a medical tool main body that is attached to a fore end of the core, and is operable by a predetermined driving force; and a containing member that is positioned at a fore end of the outer tube and, contains the medical tool main body when the medical tool main body is inserted into the body.

In addition, the medical tool is configured such that by moving the outer tube relative to the core, the containing member is made to approach the medical tool main body which is released out of the containing member in the target site in the body, thereby applying the driving force on the medical tool main body.

In doing so, the containing member not only contains the medical tool main body to convey it, but then also acts as an actuator for moving the medical tool main body, and therefore the need for inserting another actuator such as a withdrawing tube after conveying the medical tool main body through the conveying tube as has been performed can be eliminated to simplify operations and reduce the number of parts.

In order to preferably prevent the medical tool main body from being contained in the containing member as it approaches the containing member to block an actuator action, it is only necessary that along with the approaching, the containing member is compressed and deformed along the axis of the core, and the compressed and deformed containing member makes the driving force act on the medical tool main body.

It is preferable that the outer diameter of the outer tube is 0.012 inches, 0.014 inches, or 0.016 inches.

In doing so, for example, after conveying the medical tool main body to the target site, with the outer tube remaining indwelled, another medical tool such as a balloon catheter can be inserted along the outer tube to perform a surgical operation. That is, the core and the outer tube carry all functions covering the conveyance and driving of the medical tool main body, and the guidance for inserting and withdrawing other medical tools, and therefore it is only necessary to insert/remove the core and the outer tube once, thus dramatically facilitating operations for the conveyance, driving, and guidance.

Specific embodiments notably producing the effects of the present invention can include an embodiment in which: the medical tool main body is a filter member that includes a bag-like filter with an opening and is adapted to capture a free piece entering inside from the opening, such as a thrombus; and when inserted into a blood vessel, the filter member is contained in the containing member in a folded state, and when released out of the containing member in the target site in the blood vessel, placed in an unfolded state where the opening is opened, and when the containing member is made to approach the filter member by moving the outer tube forward relative to the core, the containing member makes closing force as the driving force act on the opening of the filter member.

As a more specific embodiment, the following one can be cited.

That is, the filter member further includes an elastic ring that is attached to the opening of the filter member, opens the opening by elastic restoring force of the elastic ring, and is attached to the core with multiple suspension lines that connect multiple positions of the elastic ring with a single attachment point on the core. In addition, the medical tool further includes a second tube that is wrapped around the core and is able to slide along the core, and which is located at the operating end side of the attachment point of the multiple suspension lines, in which when by moving the outer tube forward relatively to the core, the containing member is made to approach the filter member in the unfolded state, compress and deform as it pushes the second tube, the pushed second tube draws the multiple suspension lines inside, and thereby contractile force is made to act on the elastic ring of the filter member to close the opening of the filter member as well as bringing the filter member into a folded state, at which the filter member is ready to be withdrawn.

In such a configuration, in the case where the elastic ring is, at the time of being withdrawn, folded alternately away from and towards the operating end of the medical tool, forming a total of four alternating mountain and valley folds, and the portion of the elastic ring that is near to the operating end of the medical tool bites on and engulf the second tube, the portion of the elastic ring that bites on and engulf the second tube may be caught by a main catheter when pulling the filter member closer. To preferably prevent this, preferably, an outer diameter of the portion of the elastic ring that bites on and engulf the second tube, is set equal to or smaller than the outer diameter of the compressed and deformed containing member.

Also, as another specific embodiment, the following one can be cited.

The filter member further includes an elastic ring that is attached along the opening and opens the opening by elastic restoring force of the elastic ring, and is attached to the core with multiple suspension lines that connect multiple positions on the elastic ring to a single attachment point on the core. In addition, when by moving the outer tube forward relatively to the core, the containing member is made to approach the unfolded filter member that is released out of the containing member in the target site in the body, and compress and deform as it comes into abutting contact to the multiple suspension lines, as well as drawing the multiple suspension lines inside, and makes contractile force act on the elastic ring to close the opening of the filter member as well as bringing the filter member into a folded state, at which the filter member is ready to be withdrawn.

In doing so, the second tube is made unnecessary, and therefore structure can be simplified.

In the above-described configuration, in the case where the elastic ring is, at the time of being withdrawn, folded alternately away from and towards the operating end of the medical tool, forming a total of four alternating mountain and valley folds, and the portion of the elastic ring that is near to the operating end of the medical tool bites on and engulfs the second tube, the portion of the elastic ring that bites on and engulfs the second tube may be caught by a main catheter when pulling the filter member closer. To preferably prevent this, it is only necessary that in the compressed and deformed state, a substantial radius of the far side portion, relative to the operating end, of the containing member is set smaller than a substantial radius of the near side portion, relative to the operating end of the containing member. Specifically, it is only necessary that a value obtained by subtracting the substantial radius of the near side portion of the compressed and deformed containing member from the substantial radius of the far side portion of the compressed and deformed containing member is set to be equal to or larger than a wire diameter of the elastic ring.

Advantageous Effects of Invention

According to the present invention as described above, the containing member not only contains the medical tool main body to convey it, but then also acts as an actuator for moving the medical tool main body. As a result, operations can be simplified and the number of parts can be reduced.

DESCRIPTION OF EMBODIMENTS

Embodiments of the present invention will hereinafter be described with reference to the drawings.

First Embodiment

Figure 1:
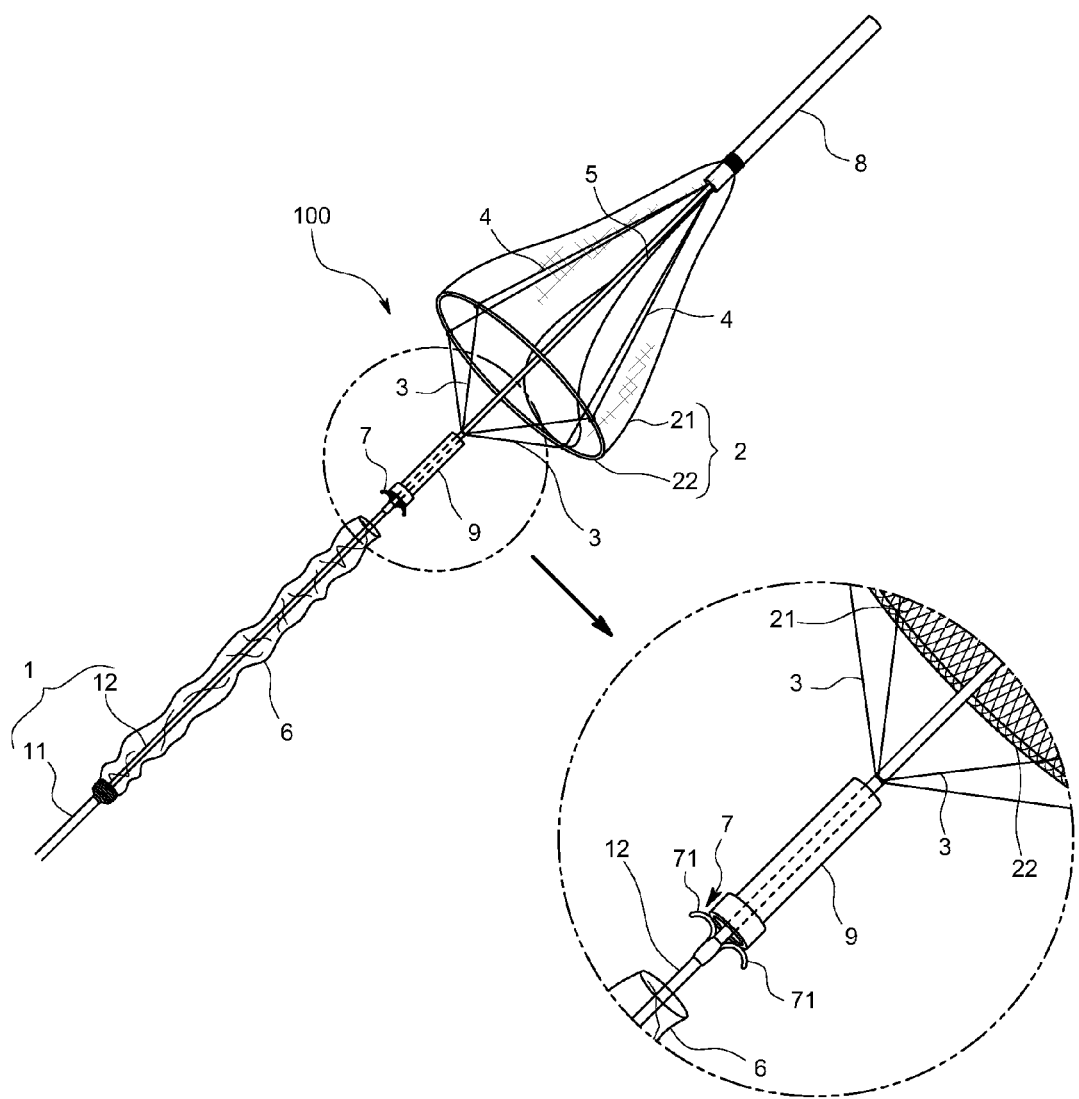
FIG. 1 is an unfolded state explanatory diagram illustrating an unfolded state of a filter member of a vascular free piece capturing tool in a first embodiment of the present invention.

An intravascular free piece capturing tool 100 as a medical tool according to a first embodiment is one that as illustrated in FIG. 1, includes: a bag-like filter member 2 having an opening; and a multifunction wire 1 for conveying and withdrawing the filter member 2 while supporting the filter member 2, as well as guiding another medical tool (such as a balloon catheter), and is configured to, at the time of a surgical operation such as providing a stent or a vascular prosthesis, make it possible to capture and withdraw a free piece A such as a thrombus detached from the inner wall of a blood vessel B by placing the filter member 2 on the downstream side of a surgical operation site in the blood vessel B.

<Configuration>

Specifically, each part of the vascular free piece capturing tool 100 is described.

The multifunction wire 1 is one that the present inventor first uses, and even though having double structure, equal in outside diameter size to a conventional single guide wire. More specifically, as illustrated in drawings such as FIG. 1, the multifunction wire 1 includes: an outer tube 11 of which the outside diameter is set to, for example, 0.014 inches that meets standards for existing general single guide wires to be inserted into a blood vessel B such as a coronary artery; and a metallic core 12 that is inserted into the outer tube 11 so as to be movable forward and backward. Note that depending on the intended use, variously sized guide wires are used; however, in general, guide wires having diameters up to 0.038 inches are used. The multifunction wire 1 of the present invention can fall within this size range.

Figure 2:
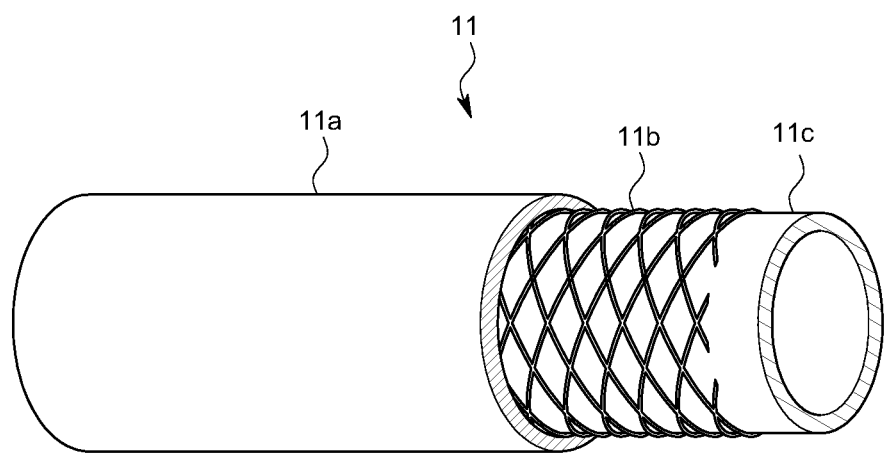
FIG. 2 is a schematic diagram illustrating an outer tube in the same embodiment.

As illustrated in FIG. 2, the outer tube 11 is one having, for example, three-layer structure and a thickness of 0.05 mm, and here, as materials for an outer layer 11a, inner layer 11b, and intermediate layer 11c, polyimide, PTFE, and material formed by weaving a metallic flat wire in a mesh-like or coil-like shape are respectively used. The length is approximately 180 cm, and regardless of such fineness, thinness, and length, the outer tube 11 is difficult to be compressed even when applying pressing force at hand, and also difficult to be expanded even when applying pulling force. That is, the outer tube 11 is configured to directly and surely transmit an operation at hand to the fore end.

In other words, the outer layer 11a made of polyimide ensures the difficulty of being compressed/expanded, whereas the inner layer 11b made of PTFE ensures smooth forward and backward movements of the core 12, and the intermediate layer 11c can promote the difficulty of being compressed/expanded with its metallic mesh and also control flexibility with its sparseness and denseness. For example, the intermediate layer 11c can also be adapted to make the fore end part of the metallic mesh sparse and flexible only by 20 cm, and the rest hard.

The filter member 2 includes: a bag-like filter 21 that is formed in a shape narrowing from the opening toward the bottom, and has an opening; and an elastic ring 22 that is attached along the opening.

The filter 21 is formed by weaving fine resin yarn in a mesh-like shape, and the surface of the resin yarn is applied with special coating on which the attachment of blood components is unlikely. Such a configuration causes the filter 21 to have characteristics of being difficult to clog and able to be placed inside a blood vessel for a period several tens of times longer than an existing filter. Note that a direction of the mesh is, as illustrated in the enlarged view in FIG. 1, adapted to be oblique to the opening edge of the filter 21.

The elastic ring 22 is one configured by winding a fine steel wire multiple times and bundling the wound wire with fine threads at multiple positions, and in a natural state where external force does not act, formed in an annular shape by elastically restoring force thereof to fulfill a function of spreading the opening of the filter 21. In this embodiment, an excess part 5 of the wound fine steel wire is spirally extended into the filter 21, and the tip part of the excess part 5 is sewed or bonded to the core 12. The excess part 5 plays a role in spreading the filter 21. In this embodiment, the excess part 5 fixes the filter 21 so as to extend along a virtual line from the top of an upward part (illustrated in FIG. 11) of the elastic ring 22 toward the bottom of the filter 21, and thereby prevents the filter 21 from being depressed inward.

The filter member 2 having such a configuration is attached, through a plurality of (four in this embodiment) suspension lines 3, to the core 12 protruded from the fore end of the outer tube 11.

Specifically, the core 12 is arranged so as to pass through the elastic ring 22 (the opening of the filter 21) and penetrate through the bottom part of the filter 21. Also, the base end parts of the respective suspension lines 3 are gathered in and fixed to one position of the core 12, from which the suspension lines 3 radially extend, and the respective tip parts are attached to four positions at which the elastic ring 22 is substantially divided.

Further, in an unfolded state where the elastic ring 22 is spread and formed in the annular shape, as illustrated in drawings such as FIG. 1, the suspension lines 3 radially spread from the one position of the core 12 toward the downstream side of blood flow, like parachute strings, and support the filter member 2 so as to make an opening face of the filter member 2 substantially orthogonal to the core 12. Note that in FIG. 1, reference numeral 4 indicates auxiliary supporting wire members that are attached symmetrically to the suspension lines 3 across the elastic ring 22, which secure an attitude of the elastic ring 22 in the unfolded state as well as ensuring that the filter 21 is surely spread.

Figure 3:
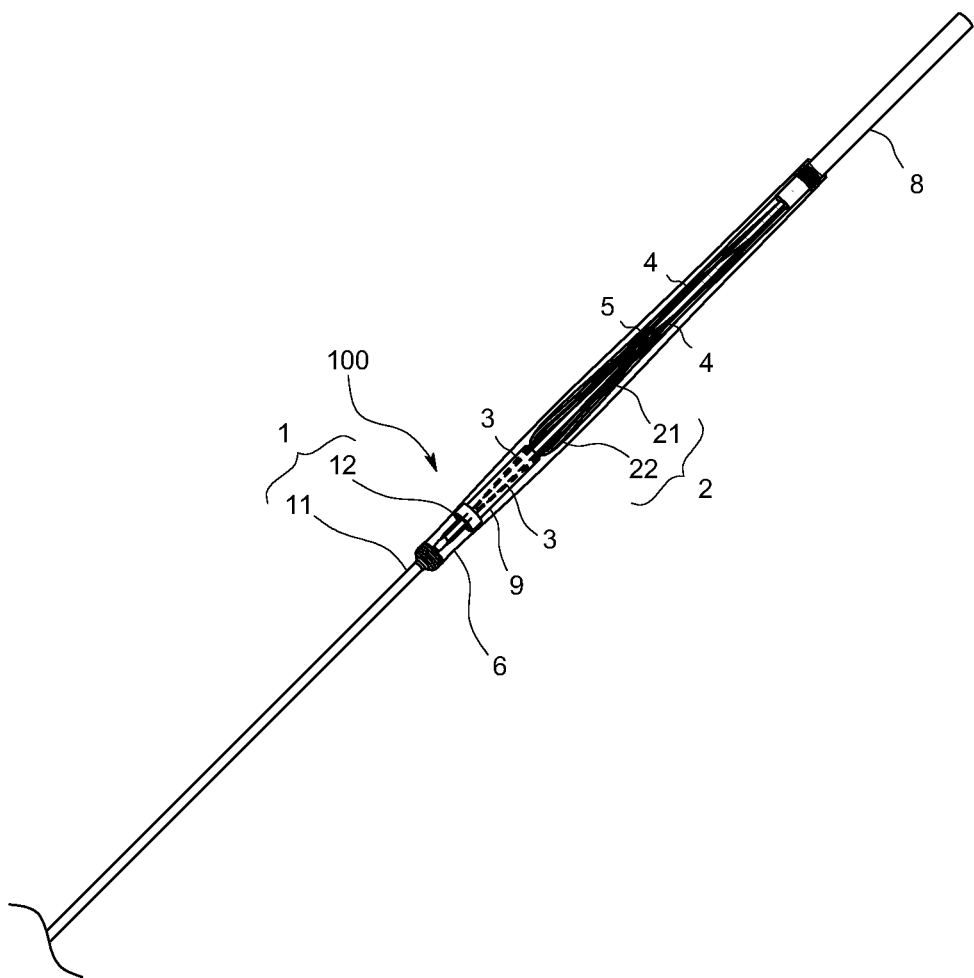
FIG. 3 is a conveyance state explanatory diagram illustrating a state in the middle of conveying the filter member contained in a containing member in the same embodiment.
Figure 11:
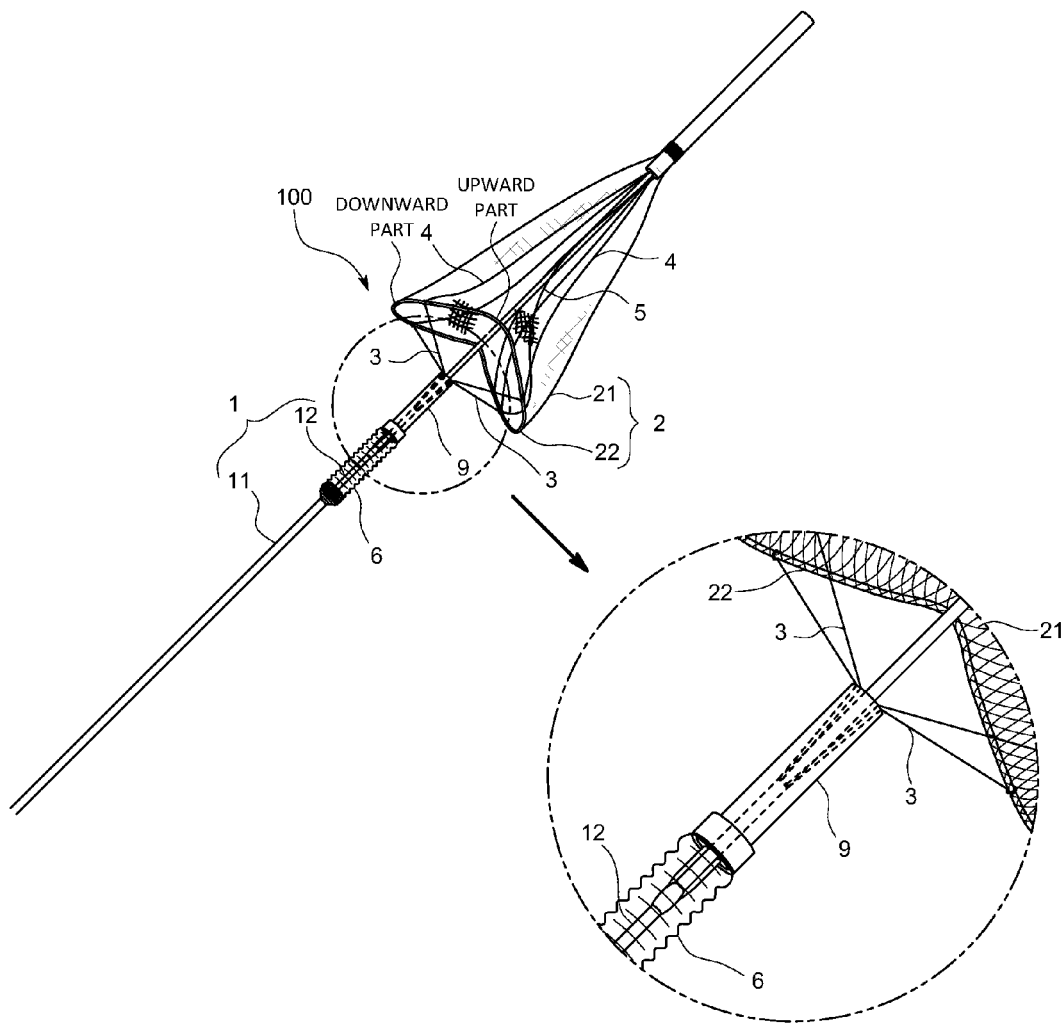
FIG. 11 is a filter member withdrawing step explanatory diagram illustrating a step of withdrawing the filter member in the same embodiment.
Figure 12:
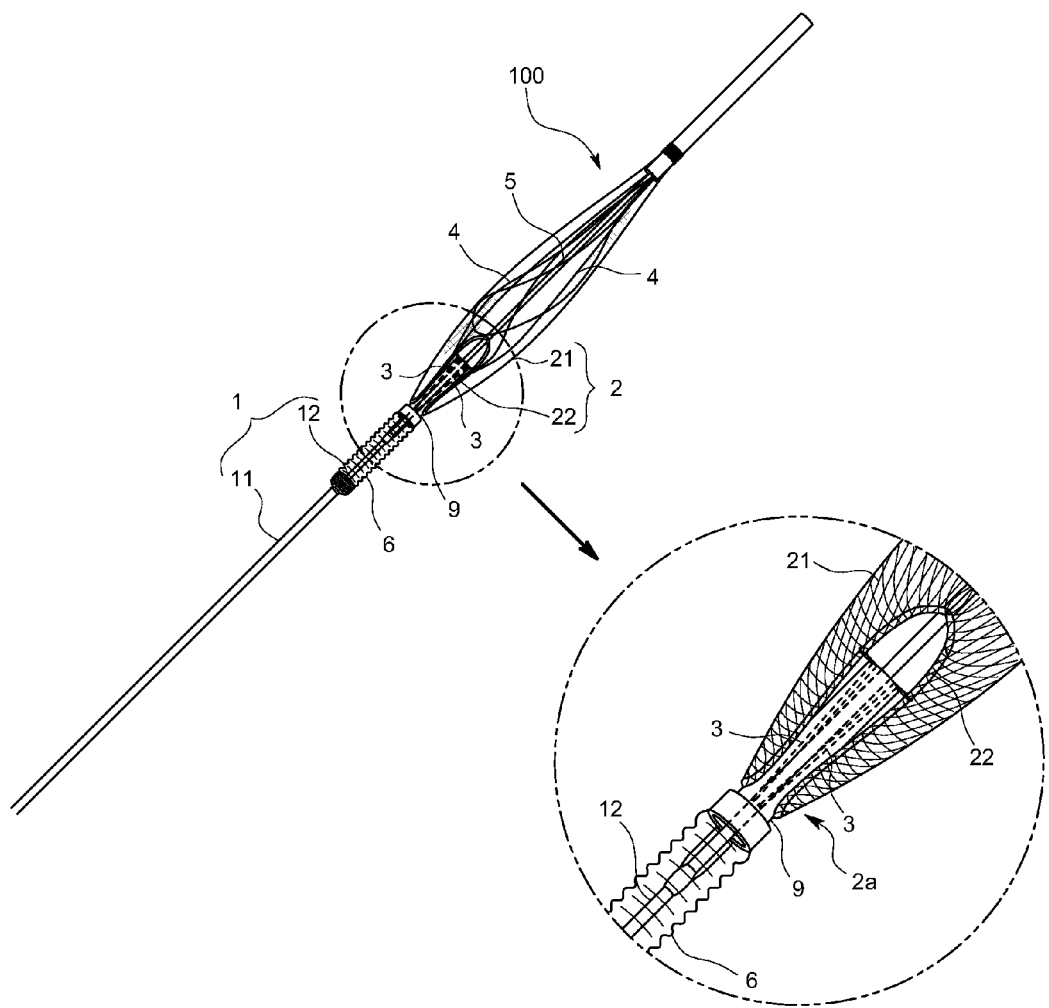
FIG. 12 is a filter member withdrawing step explanatory diagram illustrating the step of withdrawing the filter member in the same embodiment.

On the other hand, the filter member 2 is also configured to be foldable and formable in an elongated shape. That is, as illustrated in FIG. 11, the elastic ring 22 is given a tendency to easily fold alternately upward and downward at intermediate sites between any adjacent ones of the four positions where the respective suspension lines 3 are attached, and by applying external force from the circumference toward the center of the elastic ring 22 (e.g., force gathering the tip parts of the suspension lines 3 in one position), the elastic ring 22 is folded in four alternately upward and downward at the intermediate sites. As a result, as illustrated in FIG. 3 and FIG. 12, the elastic ring 22 is formed in a linear shape along the core 12, and correspondingly, the filter 21 can also be formed in the elongated shape. Such a state is hereinafter referred to as a folded state.

Note that in FIG. 1, reference numeral 8 indicates a guide tube that is attached so as to protrude from the bottom part of the filter 21, and by inserting a guide wire into the guide tube 8, the filter member 2 can be moved forward and backward while being guided by the guide wire. The guide tube 8 includes, in addition to a through-hole for a guide wire, a protection hole adapted to contain and protect the fore end part of the core 12.

Also, in this embodiment, at the fore end of the outer tube 11, as illustrated in drawings such as FIG. 1, a cylindrically-shaped containing member 6 formed of a thin film made of, for example, PTFE is attached. As illustrated in FIG. 3, the containing member 6 is a part for containing the filter member 2 in the folded state to convey the filter member 2 to a required site in a blood vessel B, and in this embodiment, preliminarily given a tendency to be compressed to easily squash in the axial direction.

Further, in this embodiment, on the operating end side of the attachment point of the suspension lines 3 on the core 12, a drive tube 9 (hereinafter also referred to as a slider 9) is slidably fitted to the outside of the core 12, and also a stopper 7 adapted to prevent the slider 9 from exceedingly separating from the filter member 2 is attached to the core 12.

When describing the respective parts, the slider 9 is one that is formed in, for example, a two-step shape of which the operating end side has a large diameter and the fore end side has a small diameter. The stopper 7 includes a pair of elastic wire members 71 extending from the core 12 toward mutually opposite sides in a branch manner, and is one that comes into contact with the end surface on the operating end side of the slider 9 to restrict the slider 9 from moving toward the operating end side. In addition, the elastic wire members 71 in this embodiment are curved in a partially arcuate shape, and when viewed as one, configured to be formed in a substantially m shape.

Further, although described later, the stopper 7 also plays a role as a compression assisting member adapted to come into abutting contact with the fore end of the containing member 6 to compress the containing member 6, and is therefore configured such that the total length of the two elastic members 71 is larger than an opening diameter of the containing member 6.

<Usage>

Next, an example of usage of the intravascular free piece capturing tool 100 having such a configuration is described below.

(First Step)

Figure 4:
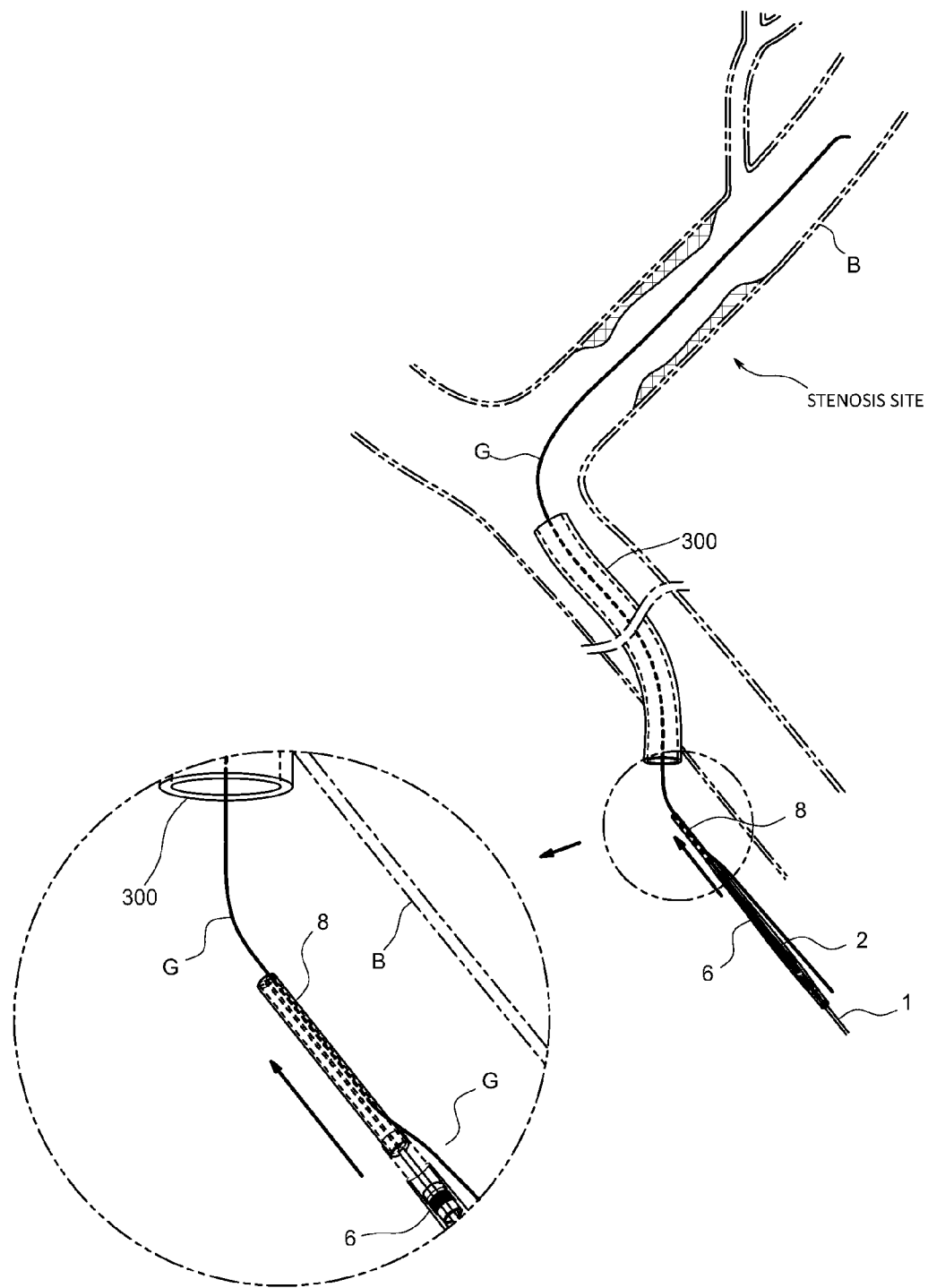
FIG. 4 is a filter member conveyance step explanatory diagram at the time of starting to insert the filter member into a blood vessel before indwelling a stent in the same embodiment.

First, as illustrated in FIG. 4, a guide wire G is inserted into a blood vessel B, and sent out to a surgical operation site (e.g., a vascular stenosis site in a coronary artery). Then, a main catheter 300 is inserted into the blood vessel B, and while being guided by the guide wire, the fore end of the main catheter 300 is positioned on the upstream side of the surgical operation site, for example, a coronary artery opening, i.e., a site at which the coronary artery branches from the aorta. Note that the guide wire G and the multifunction wire 1 have the same diameter; however, in the drawing, for easy distinction, the guide wire G is illustrated thinner. In addition, although not illustrated, at the base end of the main catheter 300, a non-return valve is typically attached. By stretching out a rubber gasket of the non-return valve, various tools such as a guide wire and a balloon catheter can be inserted.

(Second Step)

Subsequently, as illustrated in the same drawing, FIG. 4, the intravascular free piece capturing tool 100, i.e., the containing member 6 and the filter member 2 contained in the containing member 6 are inserted into the main catheter 300. When doing the insertion, as illustrated in the enlarged view of FIG. 3, the guide wire G is inserted into the guide tube 8 (the guide tube 8 is exposed from the fore end of the containing member 6) attached at the fore end of the filter member 2, and then the multifunction wire 1 is sent out. In doing so, the containing member 6 and the filter member 2 contained in the containing member 6 move forward while being guided by the guide wire G.

Figure 5:
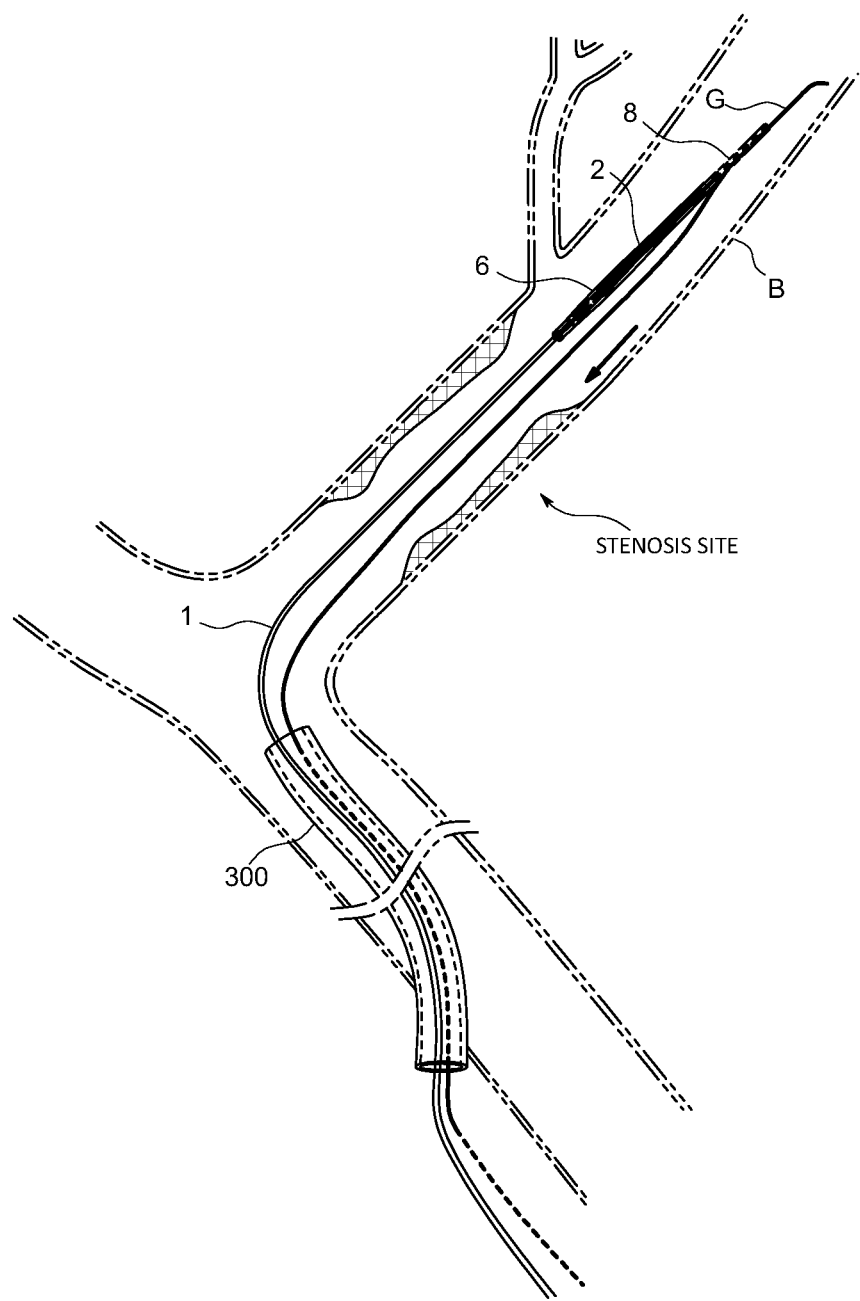
FIG. 5 is filter member conveyance step explanatory diagram illustrating a state where the filter member has been conveyed to a target site in the same embodiment.
Figure 6:
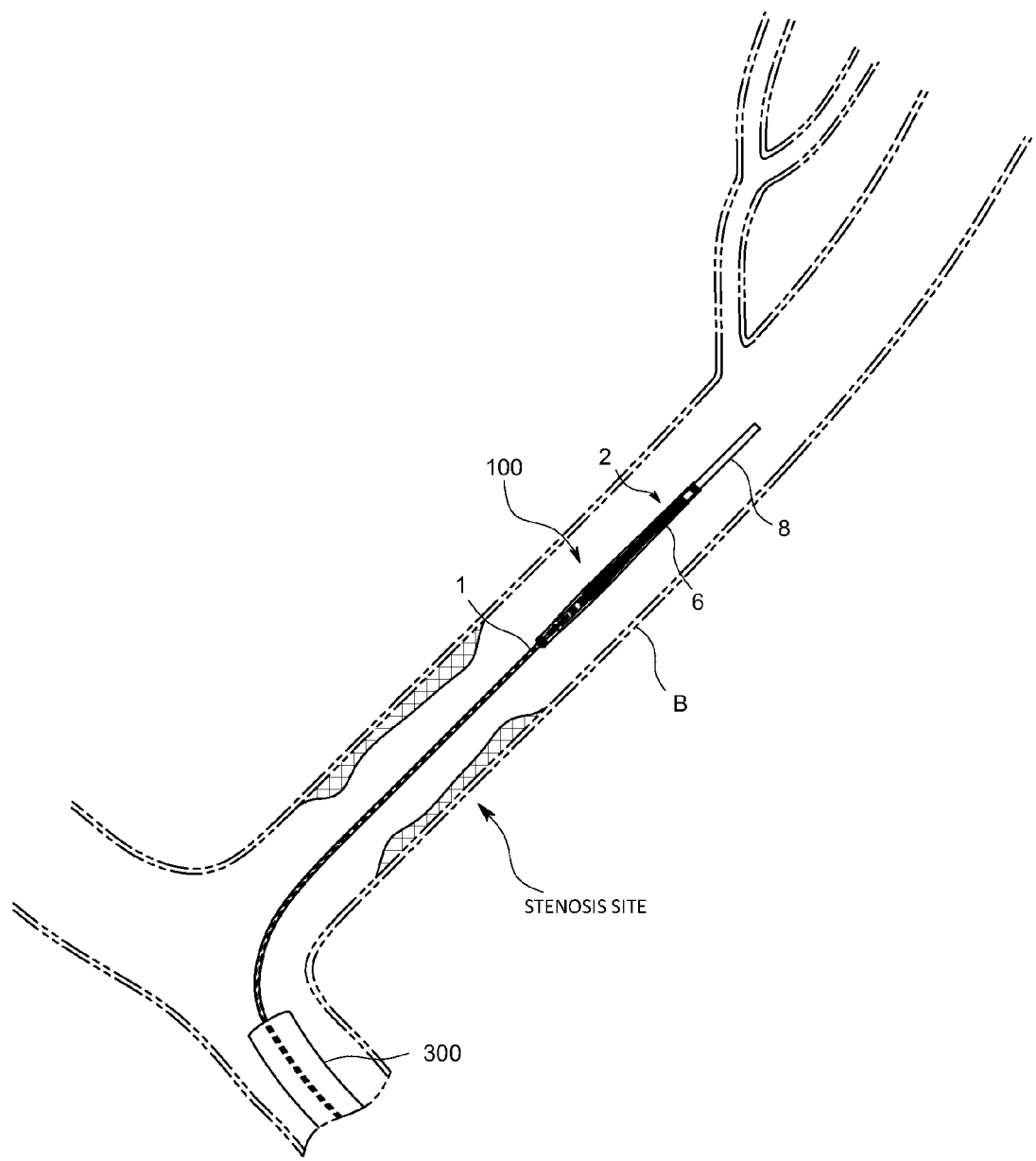
FIG. 6 is a filter member conveyance step explanatory diagram illustrating a state where the filter member has been conveyed to the target site in the same embodiment.

After that, as illustrated in FIG. 5, the containing member 6 is protruded from the fore end of the main catheter 300, moved forward inside the coronary artery, and placed in a target site that is on the slightly downstream side of the surgical operation site. Then, in this embodiment, as illustrated in FIG. 6, the guide wire G is drawn out, or alternatively may be left as it is.

(Third Step)

Subsequently, without moving the core 12 of the multifunction wire 1, only the outer tube 11 is moved backward a predetermined distance by an operation at hand. In doing so, as illustrated in FIG. 1, the filter member 2 moves out of the containing member 6, and also the restoring force of the elastic ring 22 opens the opening of the filter member 2, resulting in the unfolded state.

(Fourth Step)

Figure 7:
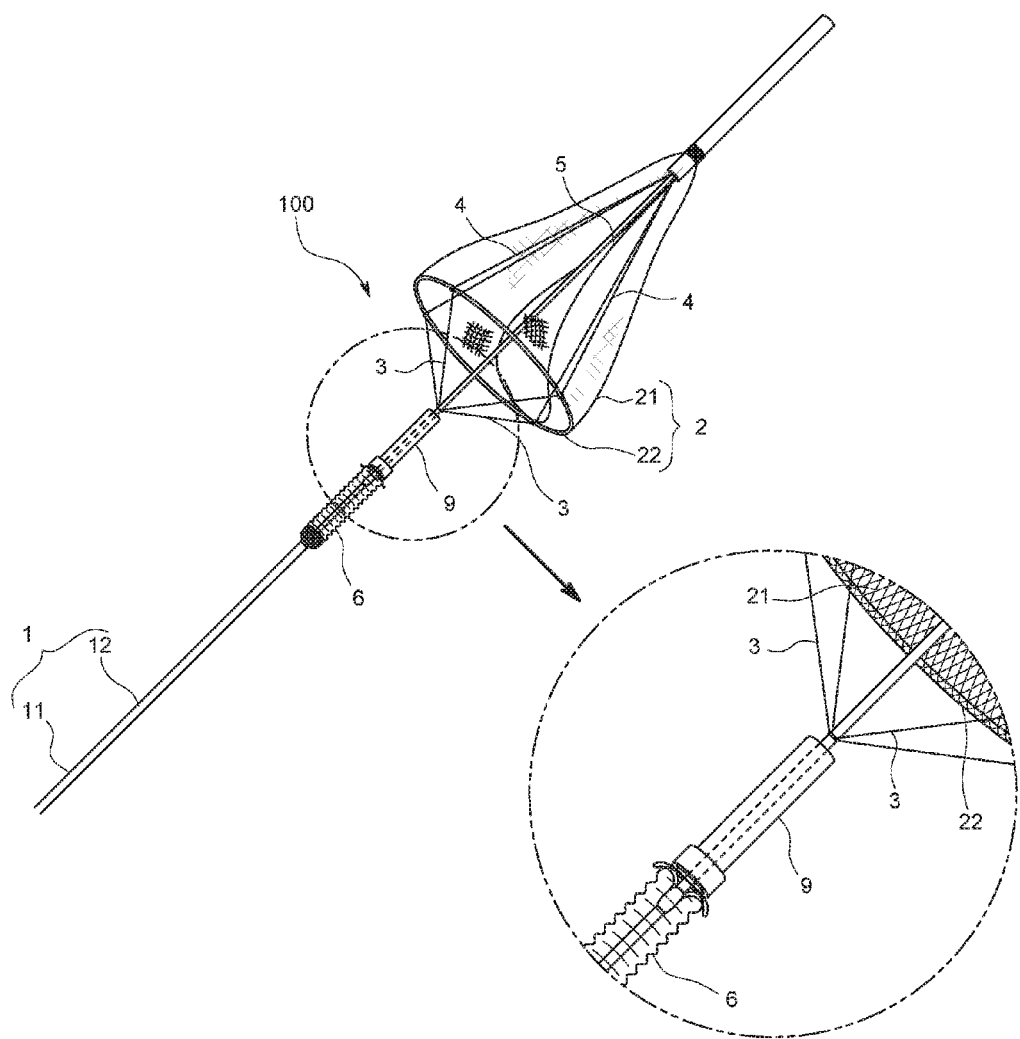
FIG. 7 is a filter member use state explanatory diagram illustrating a state where the filter member is arranged and used in the blood vessel in an unfolded state in the same embodiment.

After that, without moving the core 12, only the outer tube 11 is sent out. In doing so, the containing member 6 moves to the fore end side to come into abutting contact with the stopper 7; however, by further sending out the outer tube 11 a short distance in this state, compression force starts to act on the containing member 6 of which the fore end is stopped by the stopper 7 while the base end is pressed by the outer tube 11. In doing so, the containing member 6 is folded at multiple positions preliminarily given a tendency to fold, and as a result of shortening of the length, comes into a state illustrated in FIG. 7.

(Fifth Step)

Figure 8:
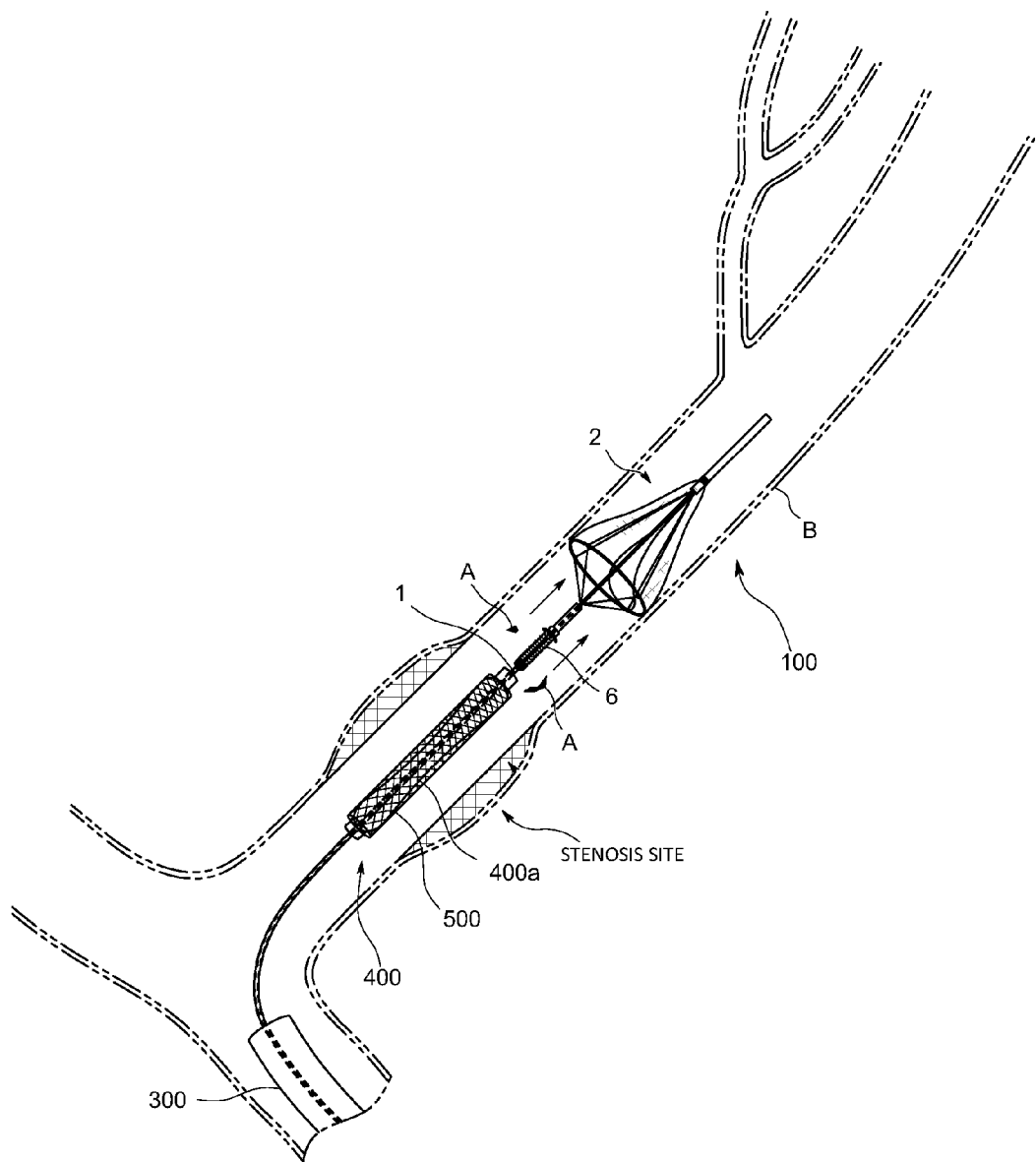
FIG. 8 is a stent indwelling step explanatory diagram illustrating a step of indwelling a stent through a balloon catheter after arranging the filter member in the blood vessel in the unfolded state in the same embodiment.
Figure 9:
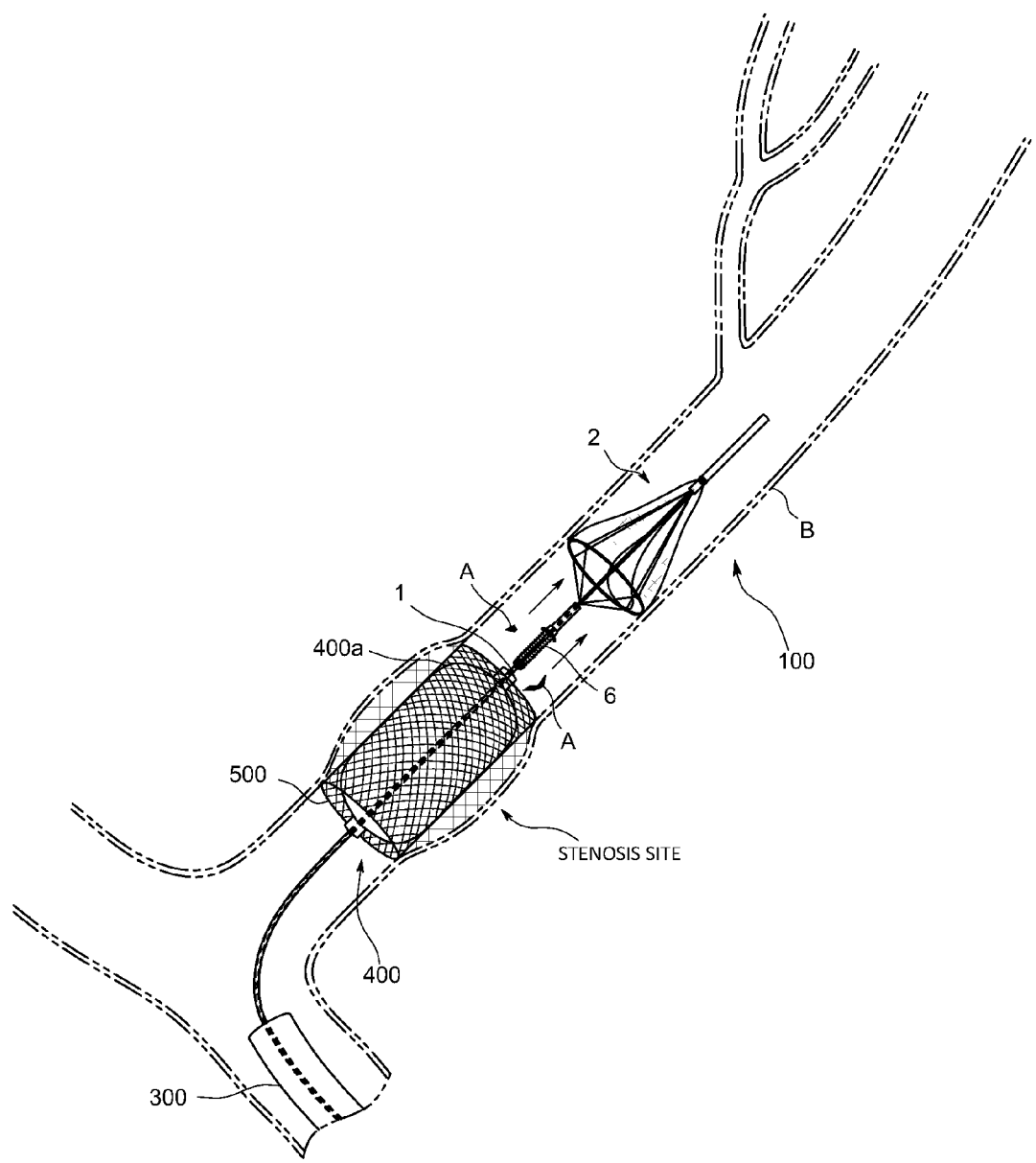
FIG. 9 is a stent indwelling step explanatory diagram illustrating the step of indwelling the stent after arranging the filter member in the blood vessel in the unfolded state in the same embodiment.
Figure 10:
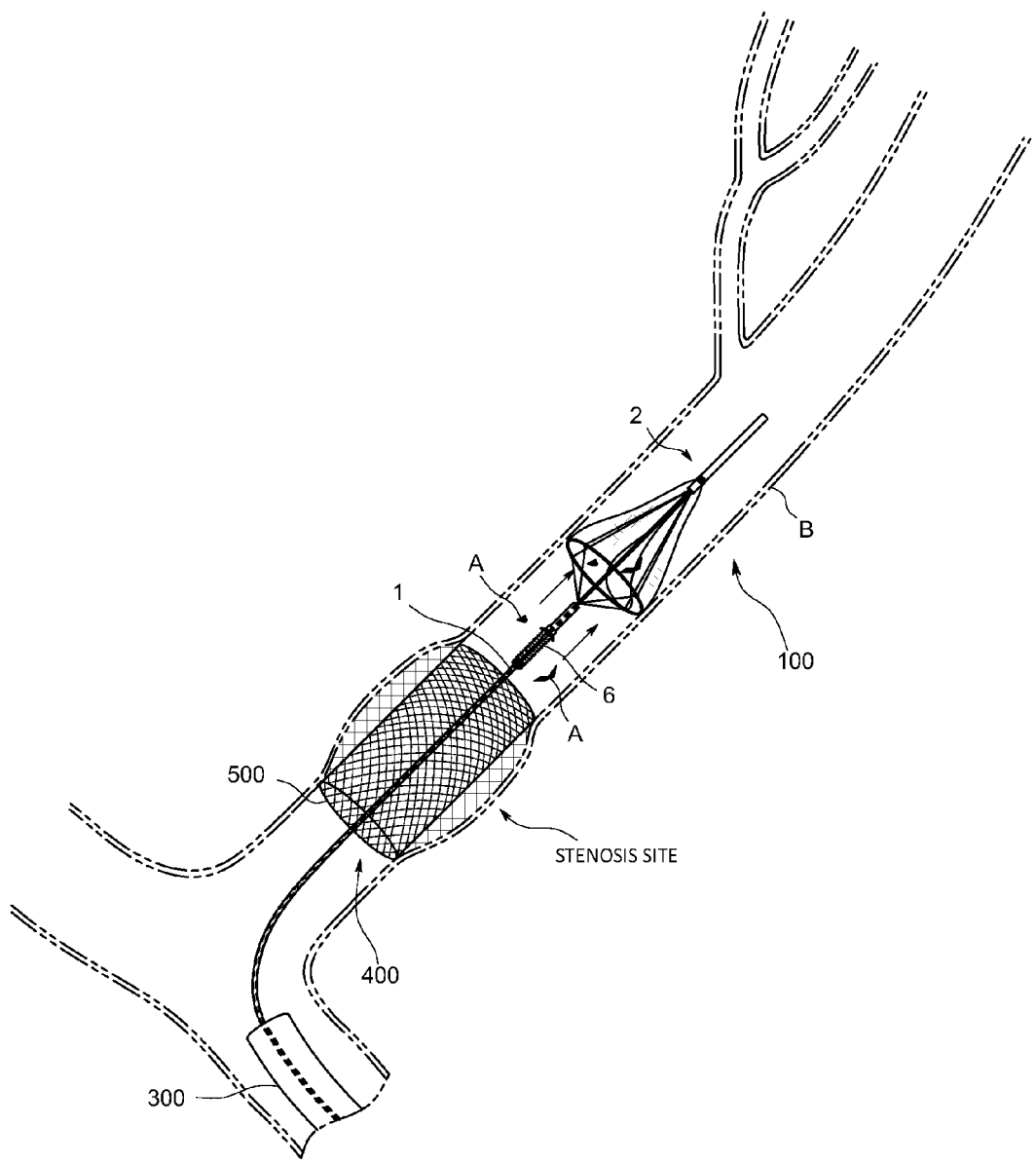
FIG. 10 is a stent indwelling step explanatory diagram illustrating the step of indwelling the stent after arranging the filter member in the blood vessel in the unfolded state in the same embodiment.

Subsequently, another medical tool, for example, a stent-equipped balloon catheter 400 is inserted into the multifunction wire 1 (outer tube 11) and pushed forward, and as illustrated in FIG. 8, a balloon 400a is arranged in the vascular stenosis site on the near side of the filter member 2 and the containing member 6. Then, as illustrated in FIG. 9, the balloon 400a is inflated in the vascular stenosis site, and a stent 500 is indwelled, after which as illustrated in FIG. 10, the balloon 400a is deflated, and the balloon catheter 400 is pulled closer and withdrawn.

(Sixth Step)

After that, without moving the core 12, only the outer tube 11 is further sent out. In doing so, as illustrated in FIG. 11, while bending the respective elastic wire members 71 of the stopper 7 along the core 12, the containing member 6 takes them, and comes into abutting contact with the slider 9 to move the slider 9 toward the filter member 2.

In doing so, as illustrated in the same drawing, FIG. 11, the slider 9 starts to draw the suspension lines 3 inside, the respective suspension lines 3 are drawn toward the core 12, and on the elastic ring 22, contractile force toward the core 12 acts at the connecting positions with the suspension lines 3. As a result, the elastic ring 22 starts to fold alternately upward and downward at the intermediate positions that are between adjacent ones of the four positions at which the respective suspension lines 3 are attached.

After that, when the respective suspension lines 3 are further drawn into the slider 9, and the tip parts of the respective suspension lines 3 are gathered in the fore end opening of the slider 9, as illustrated in FIG. 12, the elastic ring 22 is folded in the elongated shape along the extending direction of the core 12 as a whole to close the opening of the filter member 2. That is, the filter member 2 comes into the folded state of retaining a captured free piece such as a thrombus without releasing the free piece. At this time, as illustrated in the enlarged view of FIG. 12, part of the elastic ring 22 bites on and engulf the small diameter part of the slider 9. In addition, the part of the elastic ring 22, which bites on and engulf the small diameter part, is hereinafter also referred to as a biting part 2a.

(Seventh Step)

Figure 13:
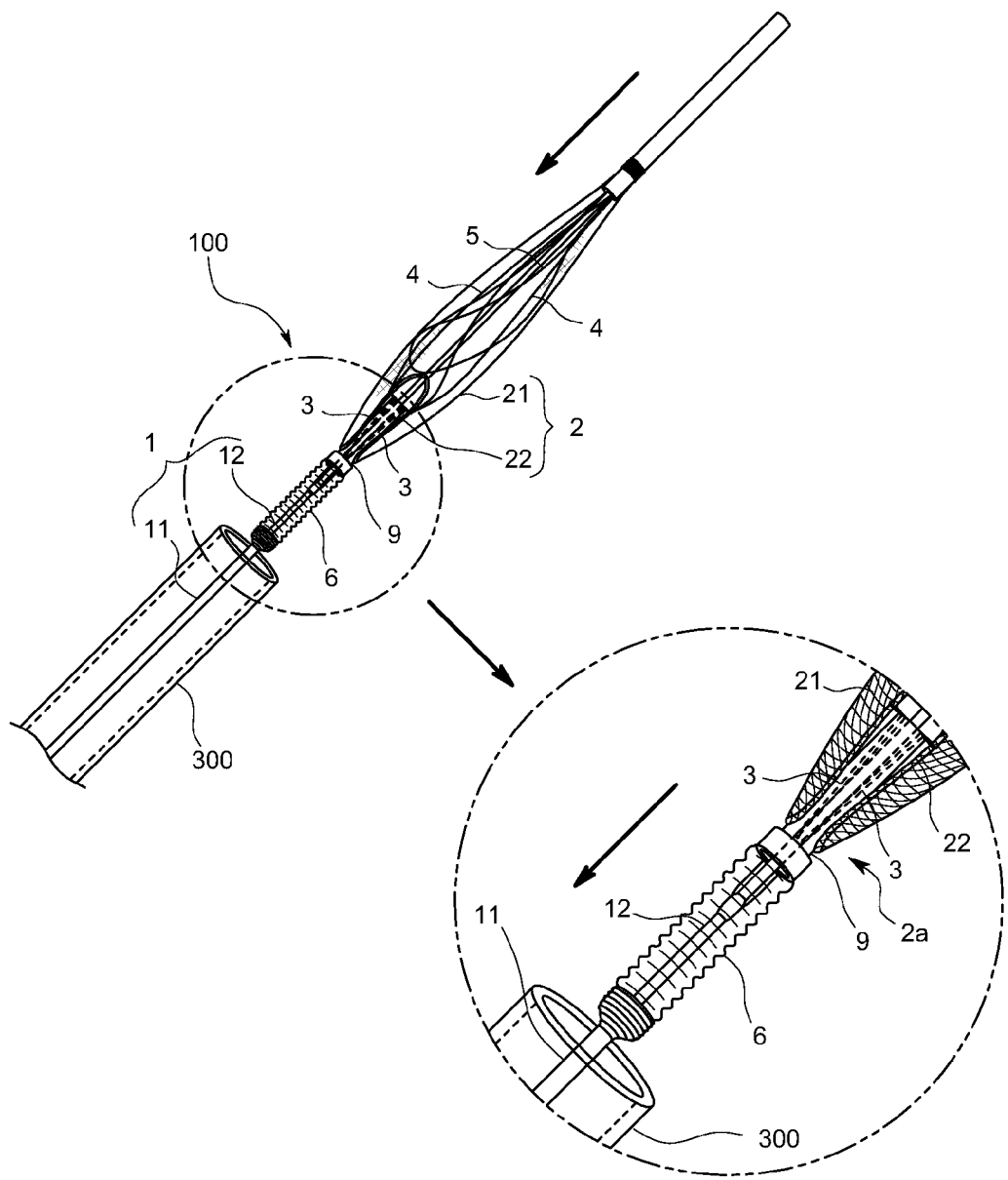
FIG. 13 is a filter member withdrawing step explanatory diagram illustrating the step of withdrawing the filter member in the same embodiment.
Figure 14:
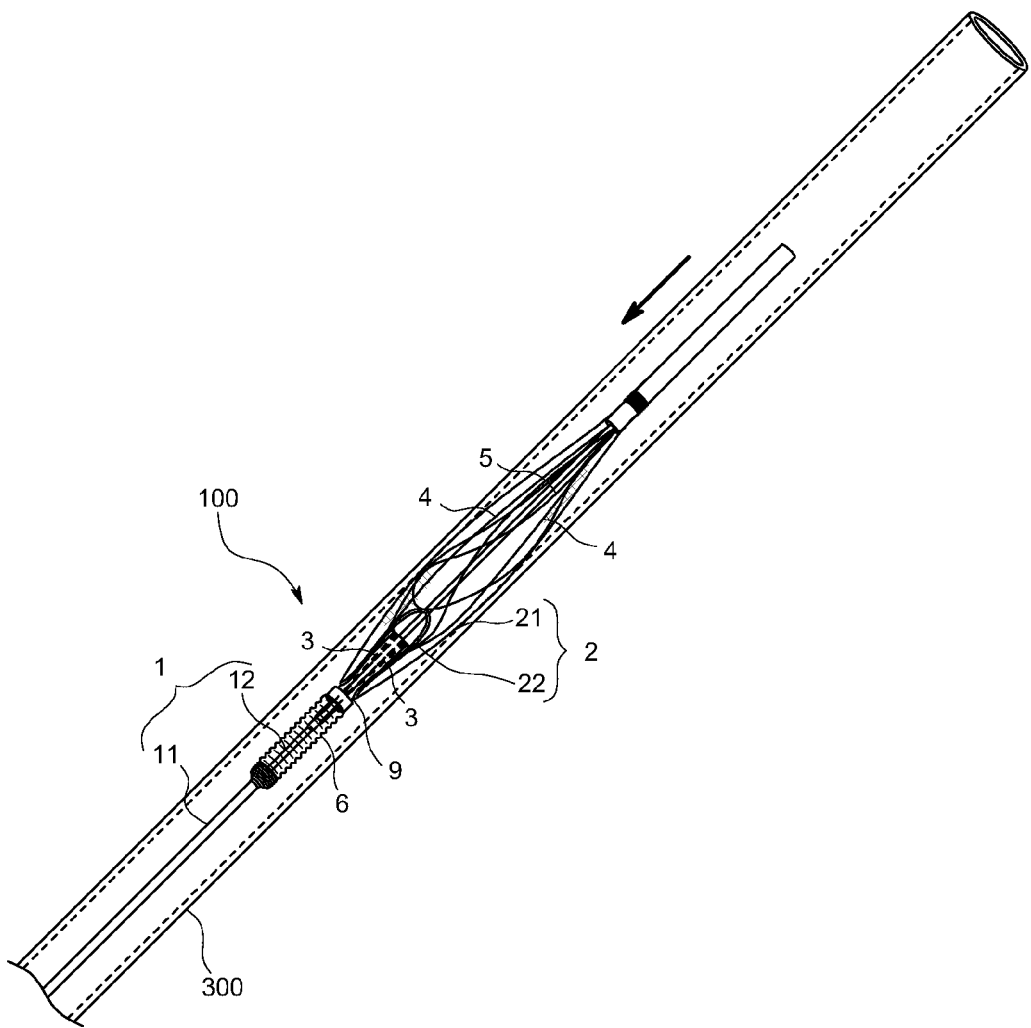
FIG. 14 is a filter member withdrawing step explanatory diagram illustrating the step of withdrawing the filter member in the same embodiment.
Figure 15A:
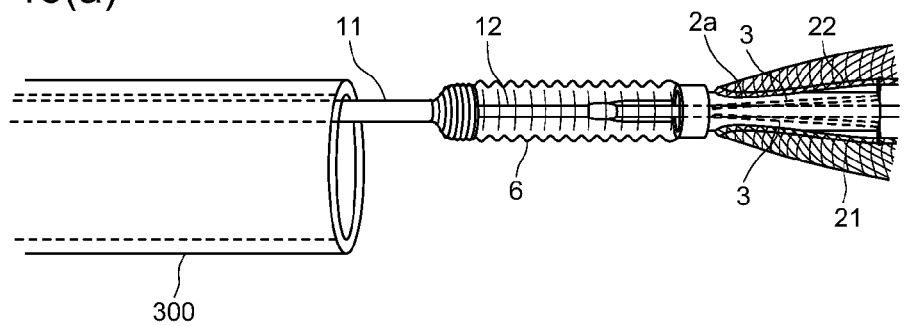
FIGS. 15(a) to 15(d) are a filter member withdrawing step explanatory diagram illustrating the step of withdrawing the filter member in the same embodiment.
Figure 15B:
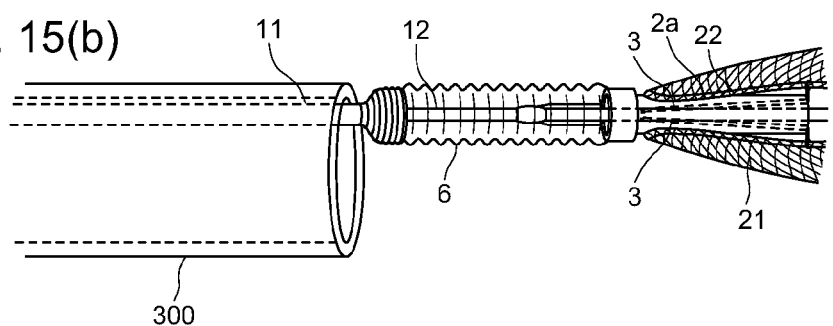
Figure 15C:
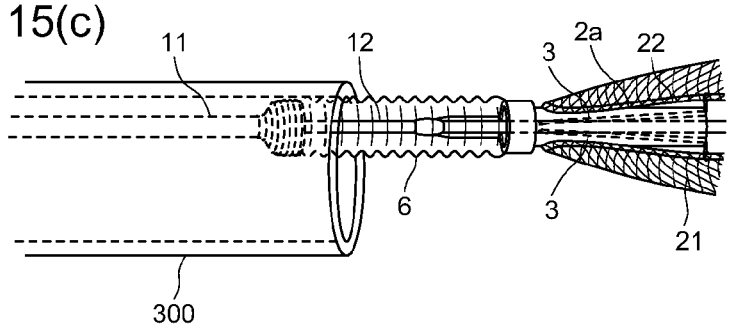
Figure 15D:
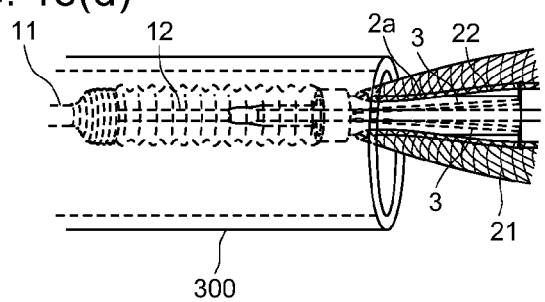

Subsequently, the multifunction wire 1 is drawn toward the operating end, and as illustrated in FIG. 13 and FIG. 14, the filter member 2 is drawn into the main catheter 300 and withdrawn. Note that in the fourth step, the balloon catheter 400 is not withdrawn, but in the seventh step, may be withdrawn together with the filter member 2. Doing so makes it possible to omit one of the series of steps.

<Effects>

The intravascular free piece capturing tool 100 according to the present embodiment configured as described employs, as a double tube structure for conveying the filter member 2 to a target site, and in the site, releasing the filter member 2 out of the containing member 6, the multifunction wire 1 having the outer tube 11 of which the outside diameter is the same in size as that of a conventional single guide wire, and therefore without withdrawing the containing member 6 and the outer tube 11 after placement of the filter member 2, makes it possible to insert a balloon catheter and the like to a surgical operation site along the outer tube 11 remaining as is to perform a surgical operation.

Further, after the surgical operation, only by slightly sending out the indwelled outer tube 11, the containing member 6 is compressed and deformed to serve as an actuator, and can thereby bring the filter member 2 into the folded state. Then, by pulling the multifunction wire 1 closer, the filter member 2 can be withdrawn.

That is, in the past, operations are complicated, such as inserting different tubes for conveying and withdrawing a filter member, whereas according to the present embodiment, the multifunction wire 1 carries all functions covering the conveyance and unfolding of the filter member 2, the guidance for inserting and withdrawing other medical tools such as a balloon catheter, and withdrawing the filter member 2, and therefore it is only necessary to insert the multifunction wire 1 once, thus dramatically facilitating operations for them.

In addition, two different tubes having been necessary for conveying and withdrawing a filter member can be replaced by the one tube. As a result, structure can be simplified, and the number of parts can be reduced.

Also, in this embodiment, as illustrated in FIG. 10, even though the stopper 7 brings the containing member 6 into the compressed state, the filter member 2 can be kept in the unfolded state, and therefore the filter member 2 can be brought closer to the balloon 400a. That is, the filter member 2 can be arranged closer to the surgical operation site such as a stenosis site, so that the possibility of arranging the filter member 2 across a branching position of the blood vessel B is reduced, and therefore the free piece such as a thrombus A can be more surely captured.

Further, in this embodiment, as illustrated in FIGS. 15(a) to 15(d), the outer diameter of the compressed and deformed containing member 6 is made larger than the size between the opposite fore end parts of the biting part 2a. As a result, even in the case where the filter member 2 is about to be eccentrically inserted into the main catheter 300 when withdrawing the filter member 2 (see FIGS. 15(a) and 15(b)), the outer edge of the containing member 6 first comes into contact with the opening edge of the main catheter 300 to push back the filter member 2 toward the centerline of the main catheter 300 (see FIG. 15(c)), and therefore the fore end parts of the biting part 2a are never caught by the opening edge of the main catheter 300. Accordingly, a situation where withdrawing the medical tool becomes difficult due to the above-described catch of the biting part 2a, or a situation where the opening of the filter member 2 is unexpectedly opened due to the catch to release the captured free piece or the like into the blood vessel can be prevented from occurring.

Next, other embodiments of the present invention will be described below. Note that regarding letters and numerals used for description and drawings in the other embodiments, members corresponding to those in the first embodiment are denoted by the same letters or numerals.

Second Embodiment

Figure 16:
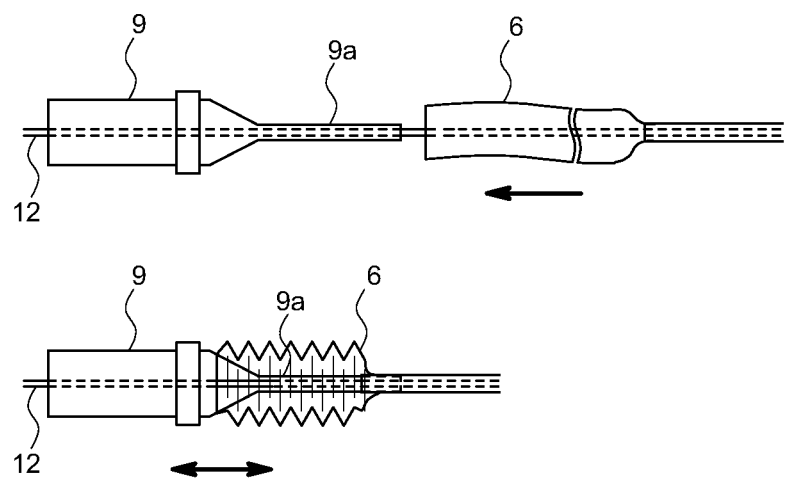
FIG. 16 is a schematic diagram illustrating a slider and a containing member in a second embodiment of the present invention.

In the second embodiment, on the base end side of the slider 9, a narrow tube 9a as illustrated in FIG. 16 is integrally provided. The narrow tube 9a is a metallic one of which the outside diameter is slightly smaller than the inside diameter of the outer tube 11. In doing so, when pressing the containing member 6 against the slider 9 to compress the containing member 6 in order to contain the filter member 2, the narrow tube 9a fits and intrudes into the fore end part of the outer tube 11, and then both of them move as one. In doing so, for example, when desiring to open/close the opening of the filter member 2 several times, by moving the containing member forward and backward by operating the outer tube, the slider 9 follows the movements, and consequently can be surely operated.

Third Embodiment

Figure 17:
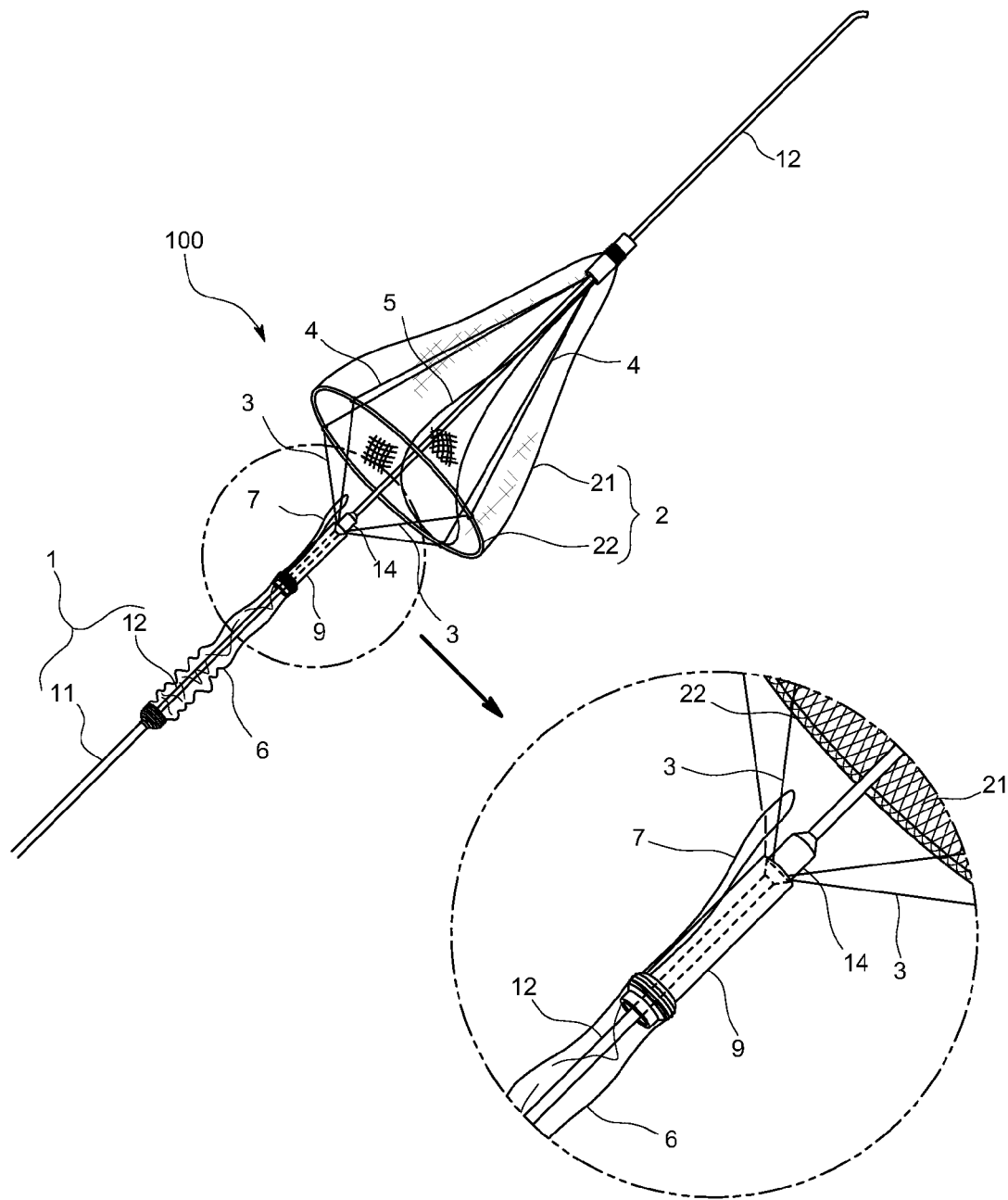
FIG. 17 is an unfolded state explanatory diagram illustrating an unfolded state of a filter member in a third embodiment of the present invention.

In the third embodiment, as illustrated in FIG. 17, as the stopper, a separation preventing thread 7 laid between the suspension lines 3 and the slider 9 is used.

Note that the separation preventing thread 7 does not have a function as the compression assisting member that is adapted to compress the containing member 6 as described in the first embodiment, and therefore in the third embodiment, near the position of the core 12 where the base end parts of the suspension lines 3 are attached, a lock part 14 having an outside diameter that is the same as or slightly larger than the inside diameter of the slider 9 is securely provided.

Figure 18:
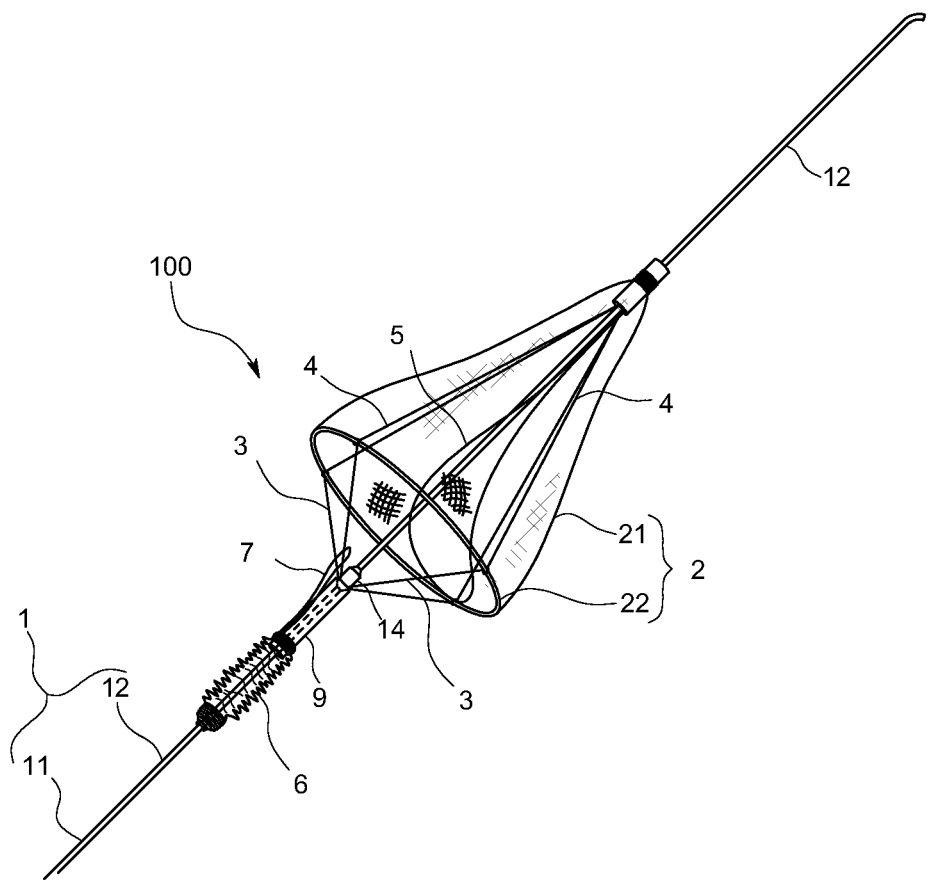
FIG. 18 is a filter member use state explanatory diagram illustrating a state where the filter member is used in the unfolded state in the same embodiment.

When only the outer tube 11 is sent out without moving the core 12, and the containing member 6 pushes the slider 9 toward the suspension lines 3, as illustrated in FIG. 18, the slider 9 first comes into contact with the lock part 14, and the movement of the slider 9 is blocked. Accordingly, by further sending out the outer tube 11 in this state, the containing member 6 is compressed. The state illustrated in FIG. 18 corresponds to those illustrated in FIGS. 7 to 10 in the first embodiment. Although the containing member 6 is compressed, the filter member 2 is not given any driving force.

Figure 19:
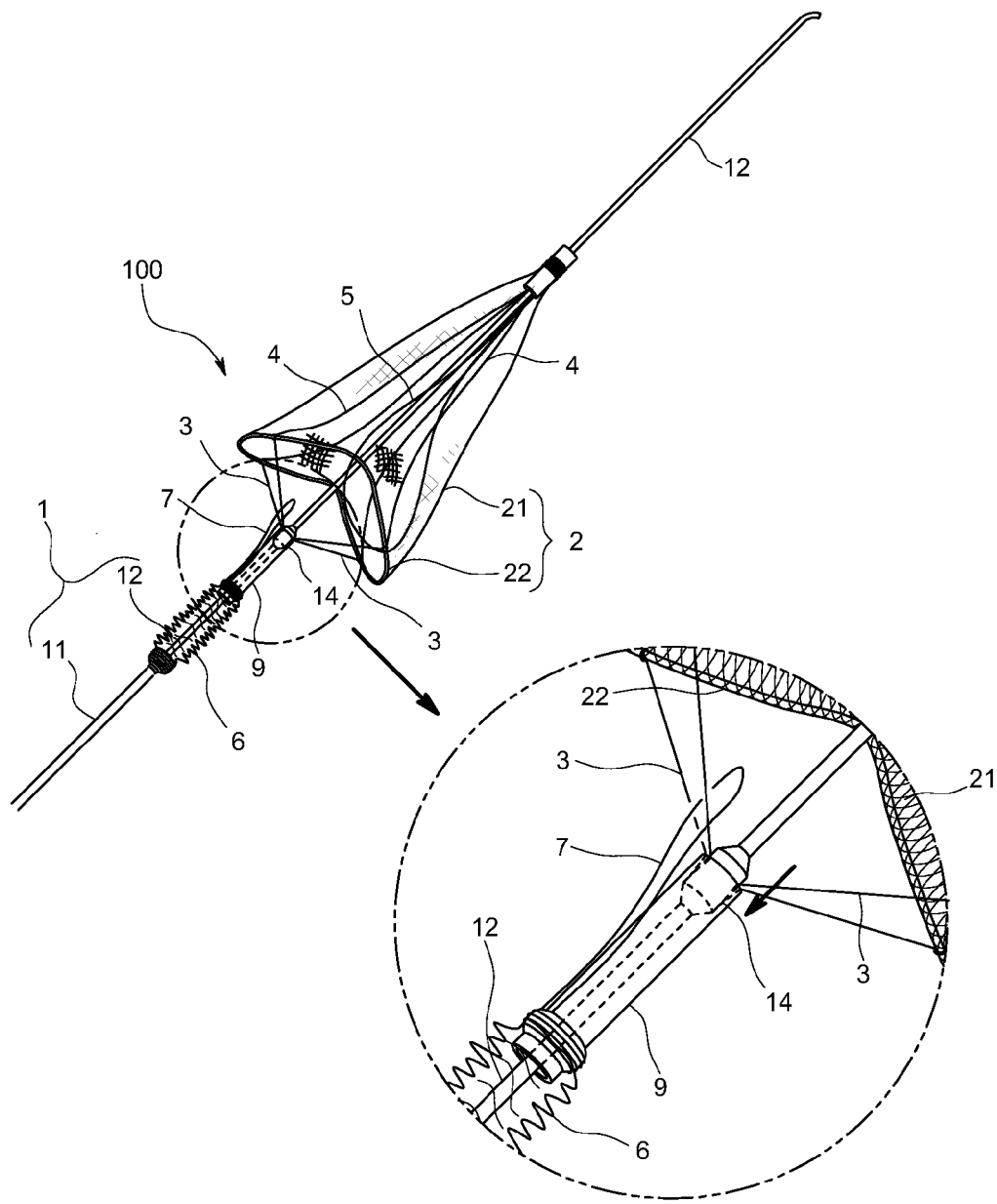
FIG. 19 is a filter member withdrawing step explanatory diagram illustrating a step of withdrawing the filter member in the same embodiment.

After that, by further sending out the outer tube 11, the containing member 6 forcibly pushes the slider 9, and consequently the slider 9 starts to move forward while drawing the lock part 14 inside. As a result, as illustrated in FIG. 19, the suspension lines 3 are drawn into the slider 9 toward the core 12. Accordingly, inward force toward the core 12 acts on the elastic ring 22 at the connecting positions with the suspension lines 3 as in the first embodiment, and the elastic ring 22 starts to fold alternately upward and downward.

Fourth Embodiment

Figure 20:
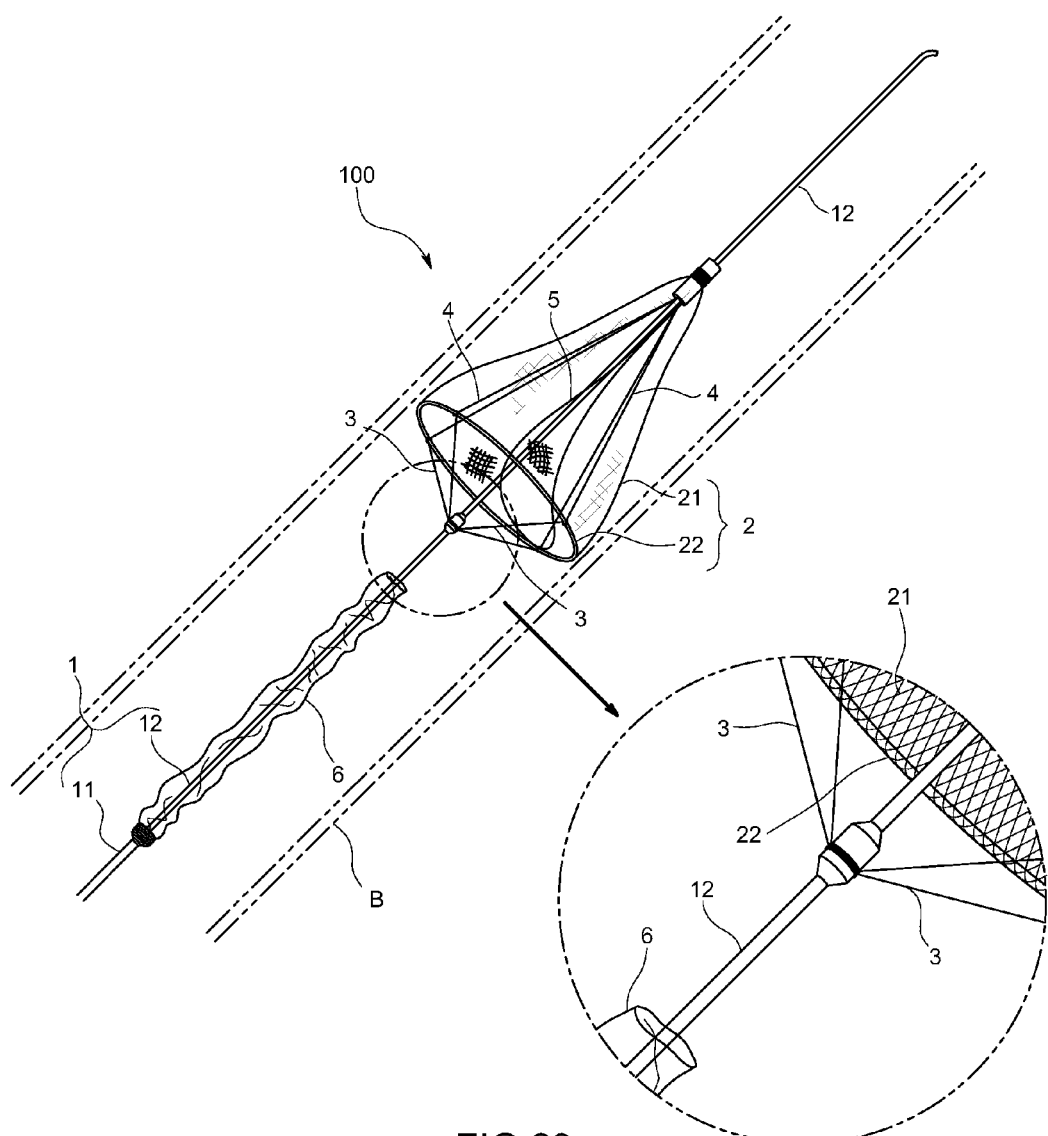
FIG. 20 is an unfolded state explanatory diagram illustrating an unfolded state of a filter member in a fourth embodiment of the present invention.

This embodiment is different from each of the above-described embodiments in that as illustrated in FIG. 20, the slider is not present, and the containing member 6 directly draws in the suspension lines 3 to bring the filter member 2 into the folded state.

A description is given specifically.

The containing member 6 is, as in the above-described embodiments, preliminarily given a tendency to be compressed in the axial direction to easily squash; however, in this embodiment, such a tendency is given, for example, in the following manner.

Figure 21:
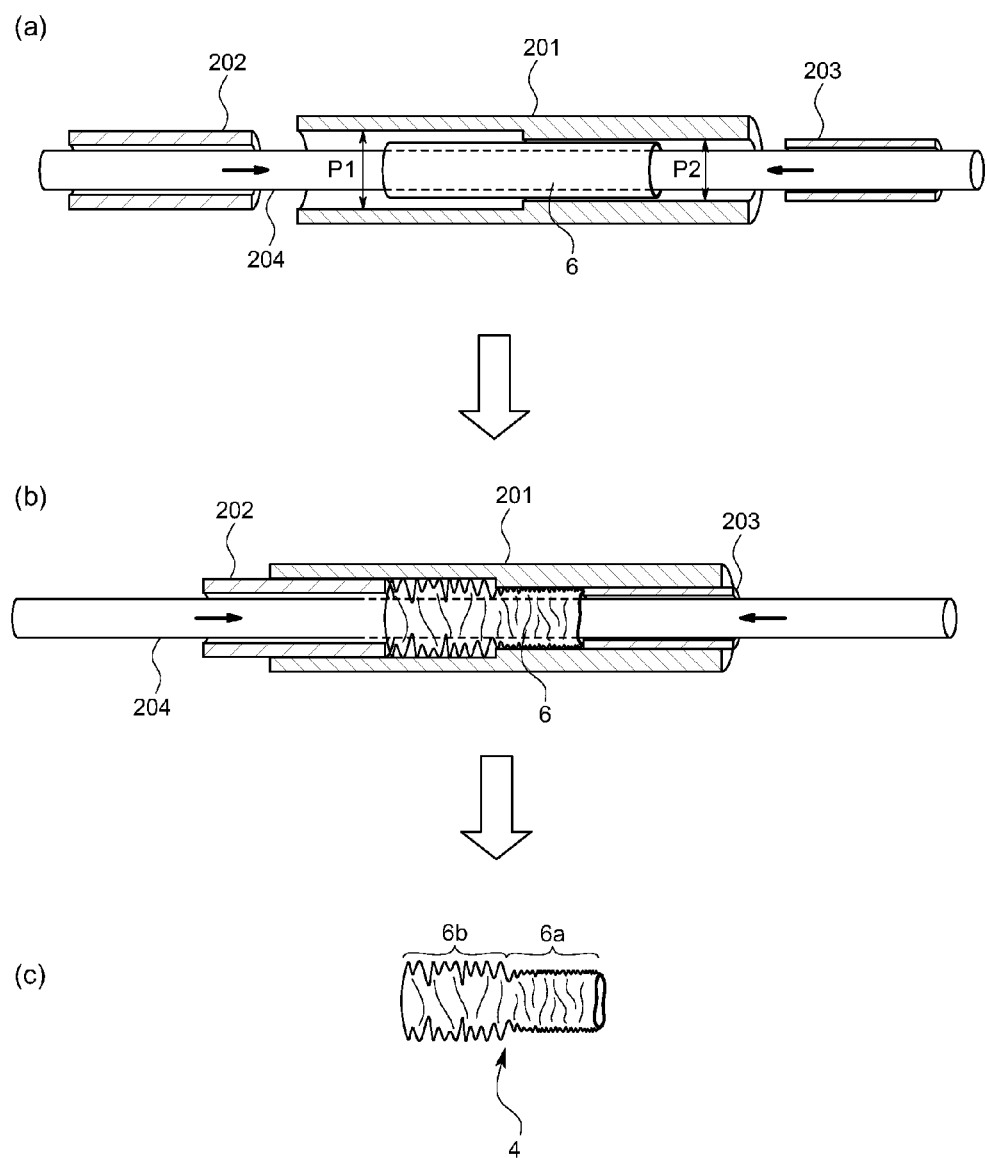
FIG. 21 is a manufacturing process explanatory diagram illustrating a manufacturing process of a containing member in the same embodiment.

First, as illustrated in FIG. 21 at (a), the containing member 6 in an uncompressed, or extended state is inserted into a tendency-giving cylindrical tube 201 having an inside diameter larger than the outside diameter of the containing member 6. In the tendency-giving cylindrical tube 201, an inside diameter P1 of the front half part thereof is a larger diameter, and an inside diameter P2 of the rear half part thereof is a smaller diameter than the inside diameter P1. At this time, as illustrated in the same drawing, a core member 204 is also inserted. The core member 204 is one of which the outside diameter is slightly larger than the outside diameter of the core 12, and ensures that when the containing member 6 is compressed, a minimum inside diameter of the containing member 6 becomes larger than the outside diameter of the core 12. In doing so, even in the compressed state, the containing member 6 can smoothly move on the core 12.

Then, as illustrated in FIG. 21 at (b) of the same diagram, from the front and rear of the tendency-giving cylindrical tube 201, a pair of compressing cylinders 202 and 203 are inserted. The front side compressing cylinder 202 inserted into the front half part has substantially the same outside diameter as the inside diameter P1 of the front half part, and the rear side compressing cylinder 203 inserted into the rear half part has substantially the same outside diameter as the inside diameter P2 of the rear half part. Thus, from the front and rear of the tendency-giving cylindrical tube 201, the pair of compressing cylinders 202 and 203 are inserted respectively predetermined distances to squash the containing member 6 in the longer direction, and in this state, the whole is heated at a predetermined temperature.

As a result, as illustrated in FIG. 21 at (c) of the same diagram, the containing member 6 is creased such that when compression force acts, a front half part thereof 6a squashes in a small diameter form, and a rear half part 6b squashes in a large diameter form larger than the small diameter form. Note that the present embodiment is adapted to make the difference in radius between the rear half part 6b and the front half part 6a equal to or larger than a wire diameter of the elastic ring 22.

In addition, the tendency-giving cylindrical tube 201 may be configured to be of a simple cylindrical shape of which the inside diameter is uniform, and prevent the containing member 6 from having the abode-described step.

Usage is substantially the same as that in each of the above-described embodiments.

However, since the slider is not present, at the time of withdrawing the filter member, the filter member 2 bites on and engulfs the compressed containing member 6 from outside.

Figure 22:
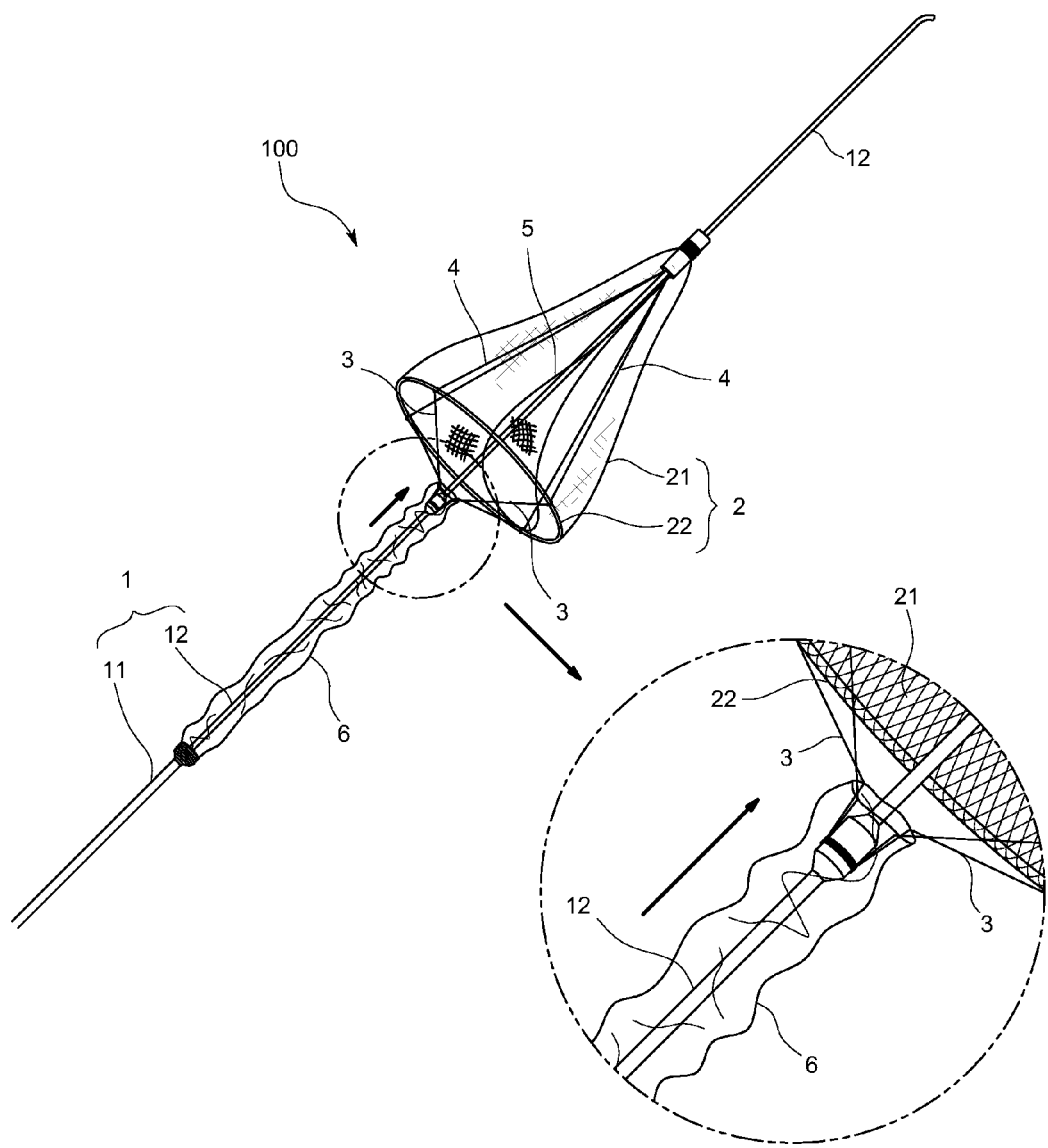
FIG. 22 is a filter member withdrawing step explanatory diagram illustrating a step of withdrawing the filter member in the same embodiment.

That is, when sending out only the outer tube 11 in the unfolded state without moving the core 12, the containing member 6 moves toward the filter member, and as illustrated in FIG. 22, the fore end of the containing member comes into contact with the base end parts of the suspension lines 3. As a result, the containing member 6 folds at a number of positions preliminarily given the tendency, and starts to be compressed.

Figure 23:
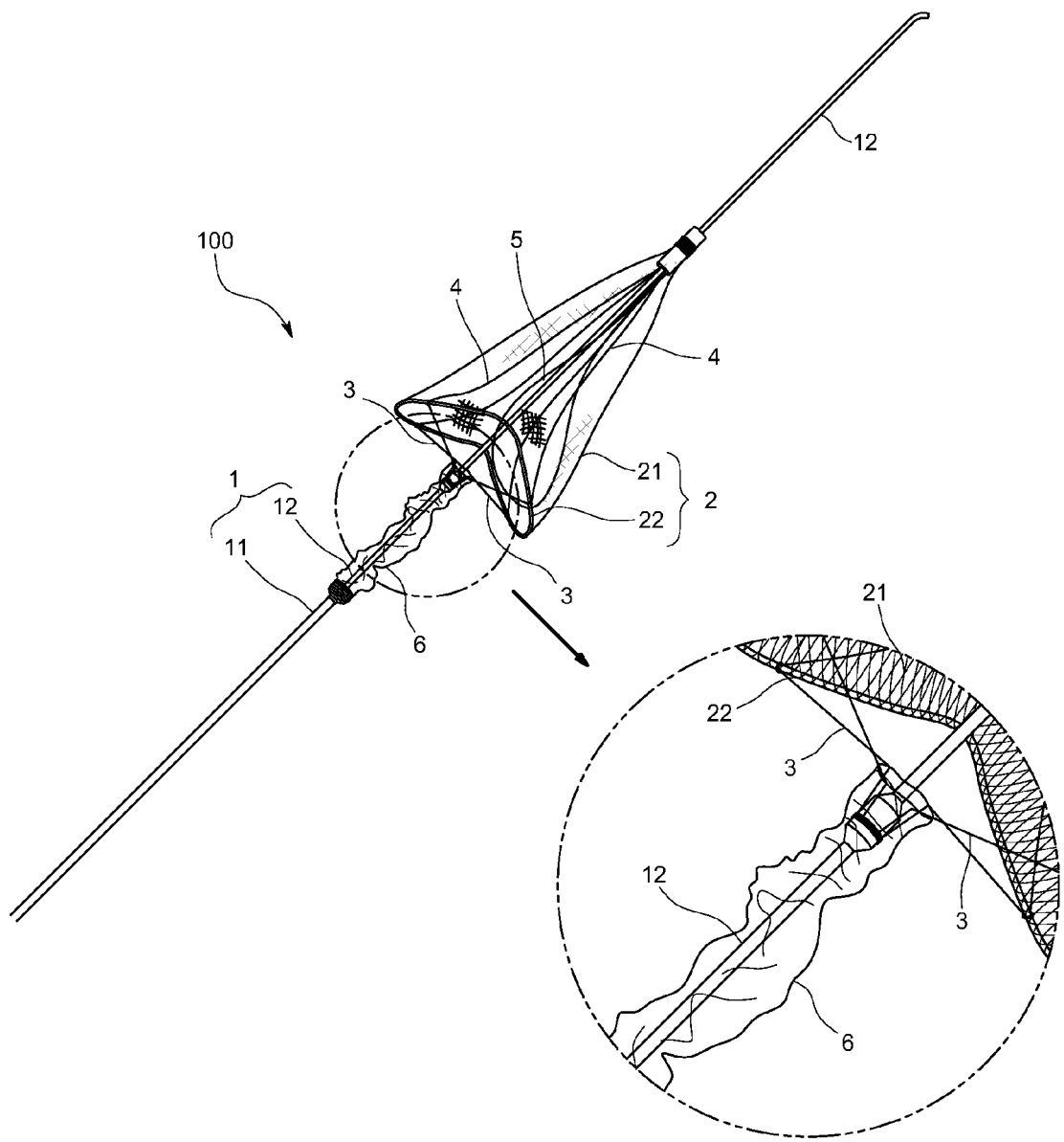
FIG. 23 is a filter member withdrawing step explanatory diagram illustrating the step of withdrawing the filter member in the same embodiment.

When compressed to some extent, as illustrated in FIG. 23, the containing member 6 starts to draw in the suspension lines 3. In doing so, the respective suspension lines 3 are drawn toward the core 12, and on the elastic ring 22, contractile force toward the core 12 acts at connecting positions with the supporting members 3. As a result, as illustrated in the same drawing, the elastic ring 22 starts to fold alternately upward and downward at intermediate sites that are between adjacent ones of the four positions at which the respective suspension lines 3 are attached.

Figure 24:
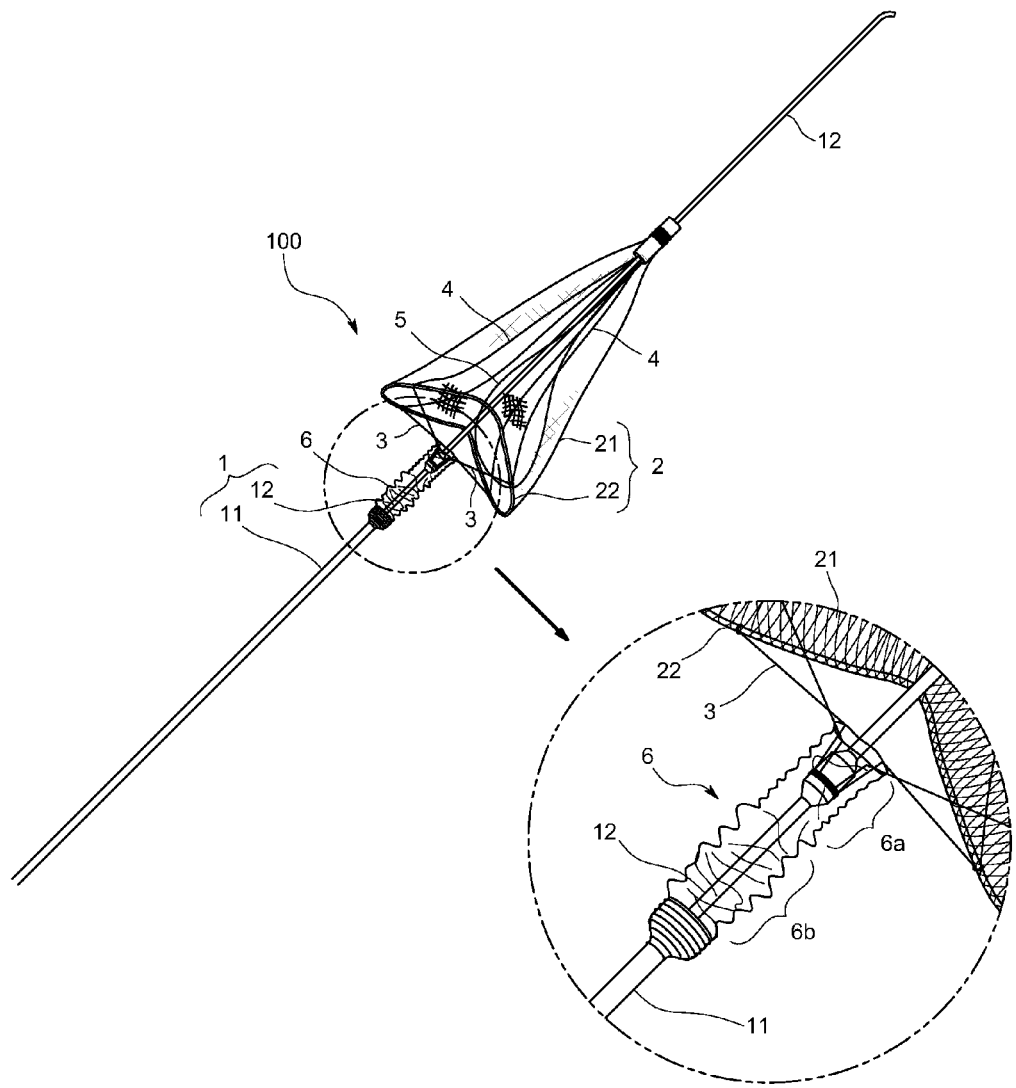
FIG. 24 is a filter member withdrawing step explanatory diagram illustrating the step of withdrawing the filter member in the same embodiment.

Then, the containing member 6 is further compressed, and as illustrated in FIG. 24, when almost completely compressed, as described above, the containing member 6 is formed in the substantially two-step cylindrical shape of which the real half part 6b is large in diameter, and the front half part 6a is small in diameter.

Figure 25:
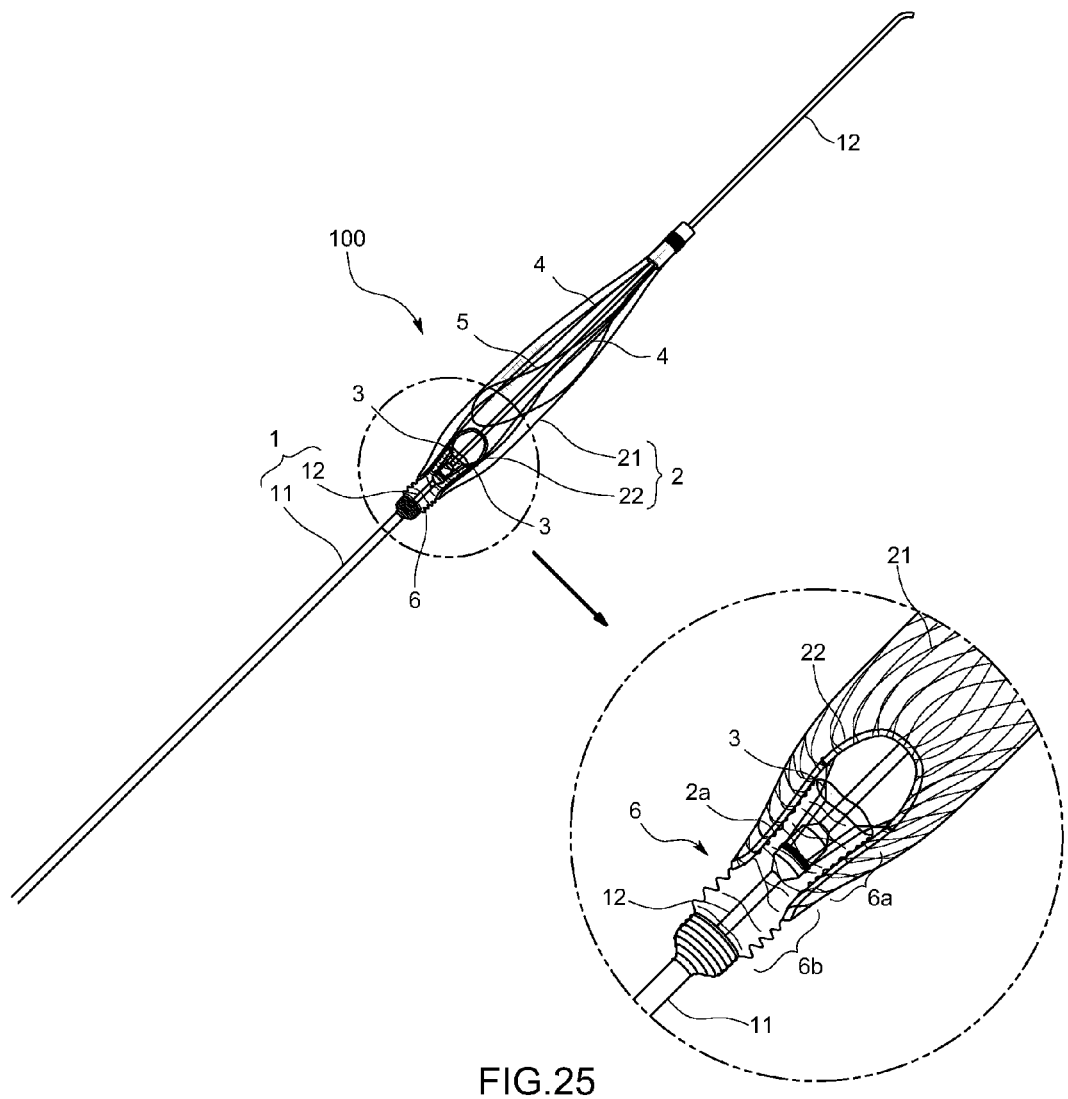
FIG. 25 is a filter member withdrawing step explanatory diagram illustrating the step of withdrawing the filter member in the same embodiment.

Subsequently, the respective suspension lines 3 are further drawn into the containing member 6, and when the tip parts of the suspension lines 3 are gathered in the fore end opening of the containing member 6, as illustrated in FIG. 25, the elastic ring 22 is formed and folded in an elongated shape along the extending direction of the core 12 as a whole to close the opening of the filter member 2. At this time, as illustrated in the enlarged view of FIG. 11, part of the elastic ring 22 bites on and engulfs the front half part 6a of the containing member 6.

A subsequent withdrawing step is the same as that in the first embodiment.

As described above, according to the fourth embodiment, as compared with the first embodiment, the number of parts can be reduced because of the absence of the slider. Also, the slider is omitted, and therefore the filter member 2 can be brought into closer to the balloon 400a correspondingly. That is, the filter member 2 can be arranged closer to a surgical operation site such as a stenosis site, so that the possibility of arranging the filter member 2 across a branching position of a blood vessel is reduced, and therefore a free piece such as a thrombus can be more surely captured.

Figure 26A:
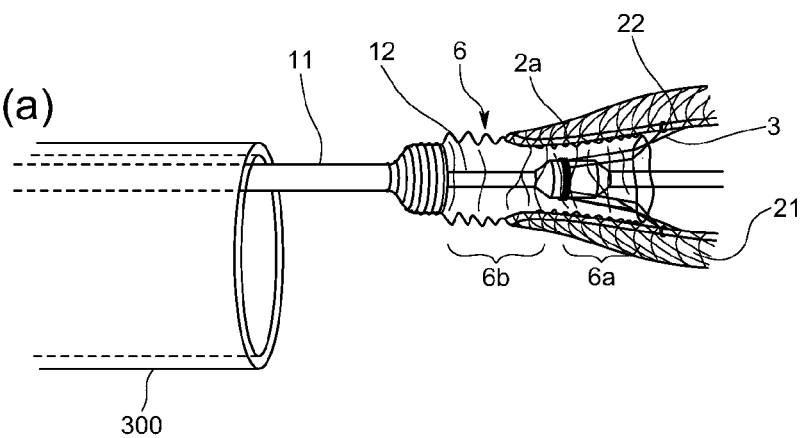
FIGS. 26(a) to 26(d) are a filter member withdrawing step explanatory diagram illustrating the step of withdrawing the filter member in the same embodiment.
Figure 26B:
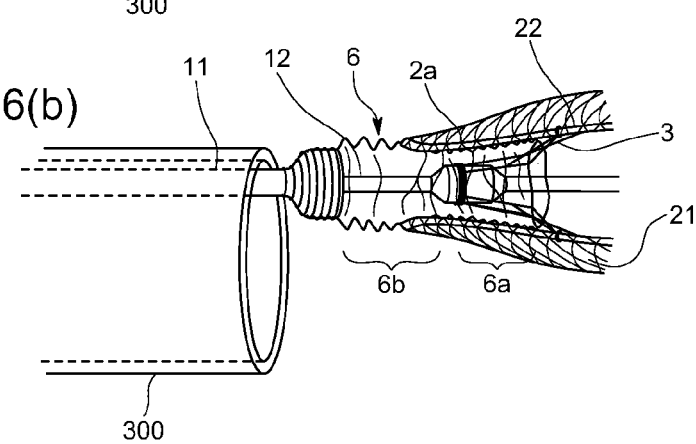
Figure 26C:
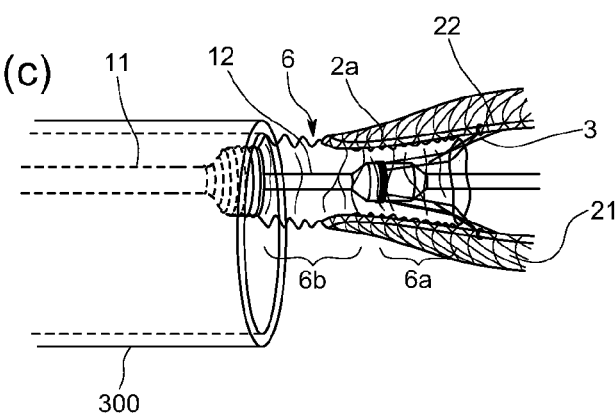
Figure 26D:
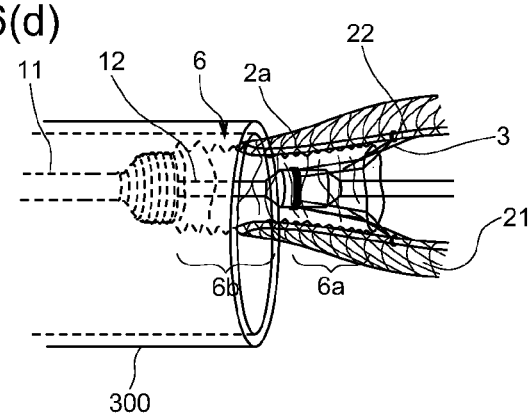
Figure 27:
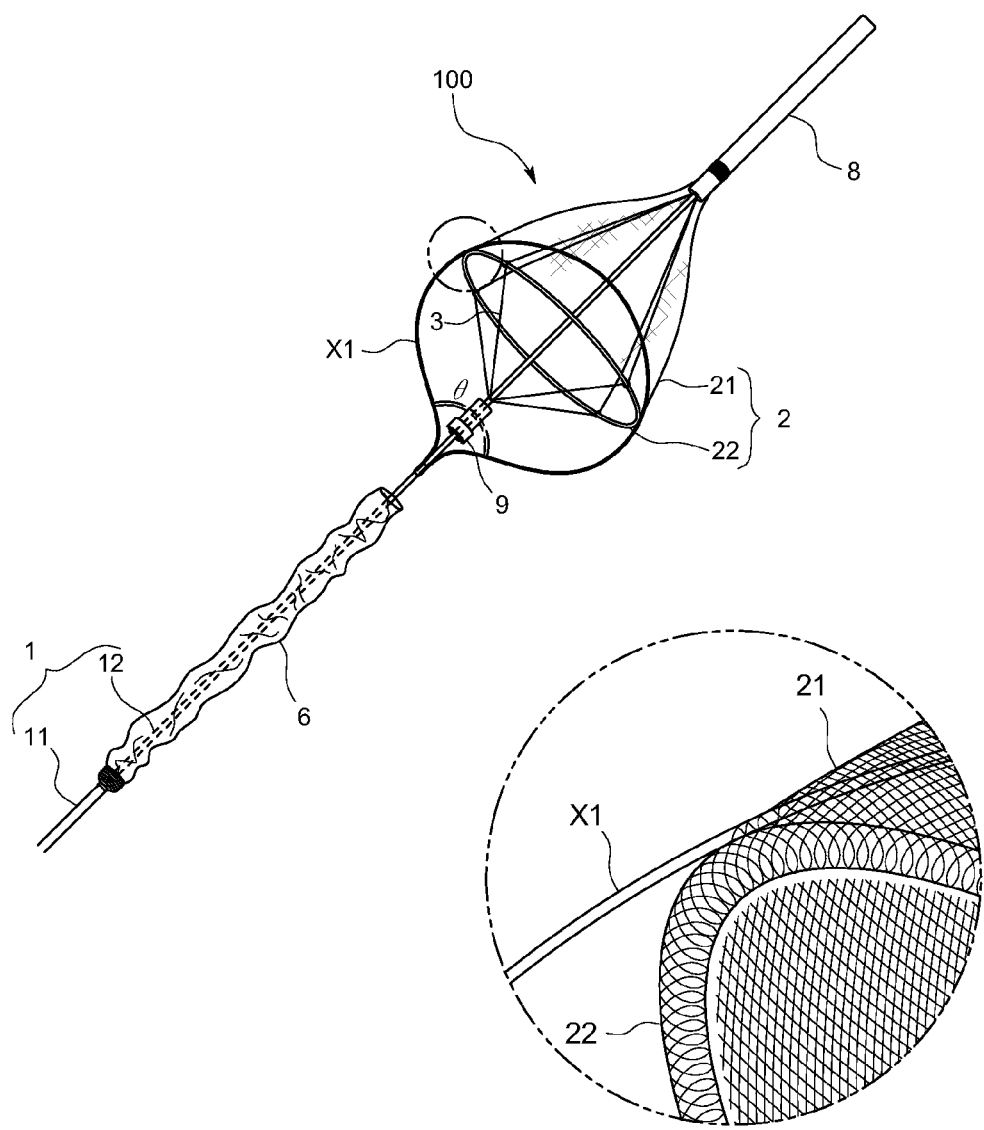
FIG. 27 is an unfolded state explanatory diagram illustrating an unfolded state of a filter member in a fifth embodiment of the present invention.

Further, since the containing member front half part 6a is small in diameter, and the elastic ring 22 bites on and engulfs the front half part 6a, as illustrated in FIG. 27, even in the case where the filter member 2 is about to be eccentrically inserted into the main catheter 300 when withdrawing the filter member 2 (see FIGS. 26(a) and 26(b)), the large-diameter rear half part 6b of the containing member 6 first comes into contact with the opening edge of the main catheter 300 to push back the filter member 2 toward the centerline of the main catheter 300 (see FIG. 26(c)), and therefore any of the fore end parts of the biting part 2a is never caught by the opening edge of the main catheter 300.

Fifth Embodiment

In this embodiment, as illustrated in FIG. 27, by fastening both end parts of an elastic wire X1 having a predetermined length to a predetermined position of the core 12, the elastic wire X1 is configured to form into a loop. In addition, two positions of the elastic wire X1 forming into the loop (hereinafter referred to as the looped elastic wire X1) are attached on the outer sides of respective downward pars of the elastic ring 22 (fore end parts of the biting part 2a) such that the looped elastic wire X1 intersects with the elastic ring 22.

Note that the looped elastic wire X1 is adapted to be able to slide in an extending direction thereof at the two attachment parts by, for example, being made to penetrate through meshes of the filter 21 (see an enlarged view of FIG. 27).

<Usage>

Next, an example of usage of the intravascular free piece capturing tool 100 having such a configuration is described below.

Usage before unfolding the filter member 2 is the same as that in the first embodiment, and therefore description thereof is omitted. Here, usage when withdrawing the unfolded filter member 2 is described.

For example, by sending out only the outer tube 11 without moving the core 12 in an unfolded state illustrated in FIG. 27, the containing member 6 is moved to the fore end side.

In doing so, the containing member 6 comes into abutting contact with a spread part at the base end part of the looped elastic wire X1. As illustrated in FIG. 27, an angle θ of the spread part (an angle on the side opposite to the containing member 6) is set to 80° to 150°, and preferably to 90° to 120°, and therefore the containing member 6 is blocked by the looped elastic wire X1 forked into two parts at a spread angle of θ. As a result, the containing member 6 does not immediately draw in the looped elastic wire X1, and the fore end thereof is suppressed by the forked spread part from moving. On the other hand, the base end of the containing member 6 is still pushed by the outer tube 11 and moves, and consequently the containing member 6 folds at a number of positions preliminarily given a tendency to fold, and starts to be compressed so as to shorten the length thereof.

Figure 28:
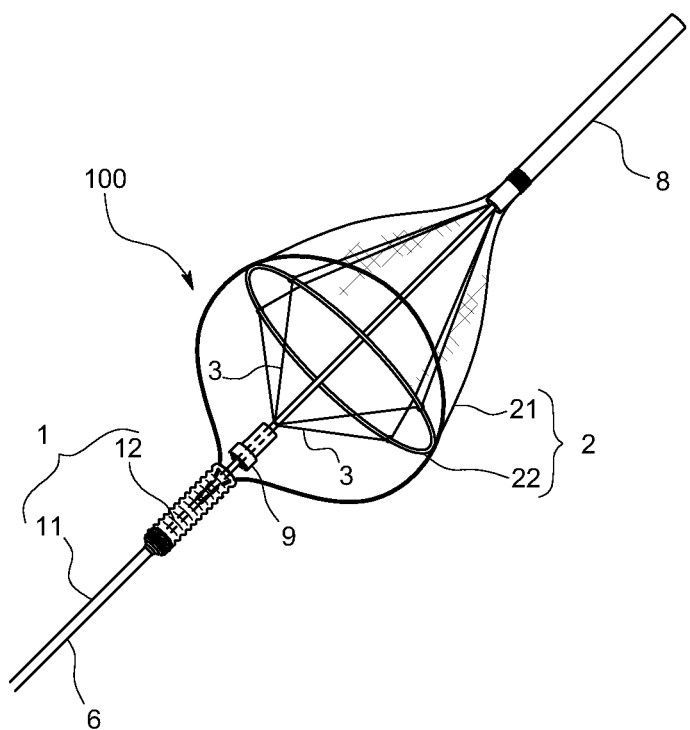
FIG. 28 is a filter member withdrawing step explanatory diagram illustrating a step of withdrawing the filter member in the same embodiment.

When further continuing to send out the outer tube 11, the containing member 6 comes into the most shortened state illustrated in FIG. 28 while drawing in the looped elastic wire X1, and then or in the process of the shortening, comes into abutting contact with the slider 9 to move the slider 9 toward the filter member 2.

Figure 29:
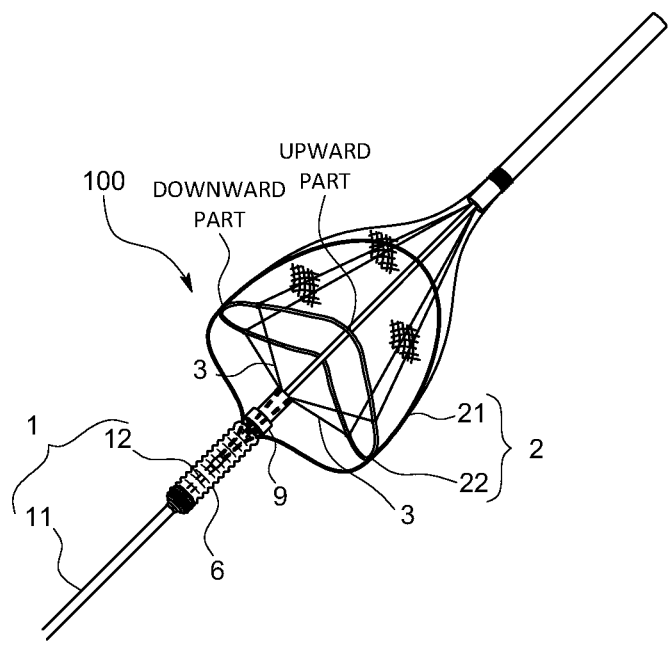
FIG. 29 is a filter member withdrawing step explanatory diagram illustrating the step of withdrawing the filter member in the same embodiment.

As a result, the slider 9 starts to draw the suspension lines 3 inside, and therefore on the elastic ring 22, contractile force toward the core 12 acts at connecting positions with the suspension lines 3 through the respective suspension lines 3. Then, as illustrated in FIG. 29, the elastic ring 22 starts to fold alternately upward and downward at intermediate positions that are between adjacent ones of the four positions at which the respective suspension lines 3 are attached.

Figure 30:
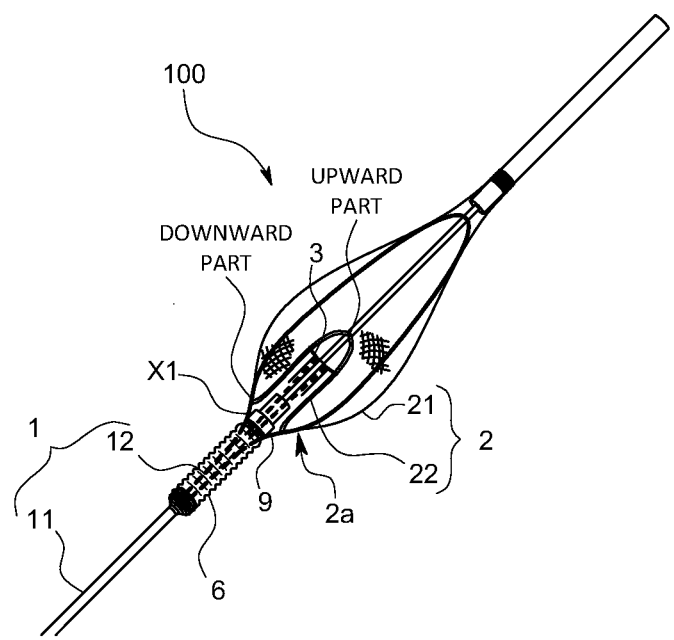
FIG. 30 is a filter member withdrawing step explanatory diagram illustrating the step of withdrawing the filter member in the same embodiment.

After that, the respective suspension lines 3 are further drawn into the slider 9, and when the fore end parts of the respective suspension lines 3 are gathered in a fore end opening of the slider 9, as illustrated in FIG. 30, the elastic ring 22 is formed and folded in an elongated shape along the extending direction of the core 12 as a whole to close an opening of the filter member 2. That is, the filter member 2 comes into a folded state of retaining a captured free piece such as a thrombus without releasing the free piece. In addition, the looped elastic wire comes into a two-fold state or a state close to the two-hold state, and part of the looped elastic wire is contained in the filter member 2.

Finally, although not illustrated, the multifunction wire 1 is drawn toward the operating end, and thereby the filter member 2 is drawn into the main catheter 300 and withdrawn.

<Effects>

As described, in the above-described configuration, as illustrated in FIG. 30, when the filter member 2 is in the folded state, the looped elastic member X1 further extends from the fore end of the containing member 6 outward in the fore end direction, and comes into a state of passing on the outer sides of the fore ends of the biting part 2a to get into the filter member 2.

As a result, even in the case where the biting part 2a is slightly opened in the folded state (actually, depending on an amount of free pieces captured in the filter member 2, the biting part 2a may not be closed enough to come into close contact with the slider completely), the opening is guarded by the looped elastic wire X1. Accordingly, for example, even in the case where the filter member 2 is about to be eccentrically inserted into the main catheter 300, and the opening of the biting part 2 is about to be caught by the opening edge of the main catheter 300, the looped elastic wire X1 blocks the opening from being caught, and pushes back the filter member 2 toward the centerline of the main catheter 300, and therefore the fore end parts of the biting part 2a are never caught by the opening edge of the main catheter 300.

In this manner, a situation where withdrawing becomes difficult due to the above-described catch of the biting part 2a, or a situation where the opening of the filter member 2 is unexpectedly opened due to the catch to release a captured free piece or the like into a blood vessel can be prevented from occurring.

Also, the angle of the spread part of the looped elastic wire X1 is set to 150° to 170°, and the containing member 6 is configured to comes into contact with the spread part and shorten before coming into contact with the slider 9, so that the containing member 6 pushes the slider in the shortened state, i.e., in a state where a minimum inside diameter is smaller than that in a lengthened state. Accordingly, a situation where the containing member 6 is fitted at the outside of the slider 9 to fail to push the slider 9 can be prevented, and the containing member 6 can surely move the slider 9 to bring the filter member 2 into the folded state.

On the other hand, at the time of placement in a required site in a blood vessel, i.e., when taking the filter member 2 out of the containing member 6, in addition to elastic restoring force of the elastic ring 22 itself, elastic restoring force of the looped elastic wire X1, which attempts to spread the looped elastic wire X1, also acts on the elastic ring 22. As a result, the elastic ring 22 can be more surely spread to ensure a better unfolded state as well.

Figure 31:
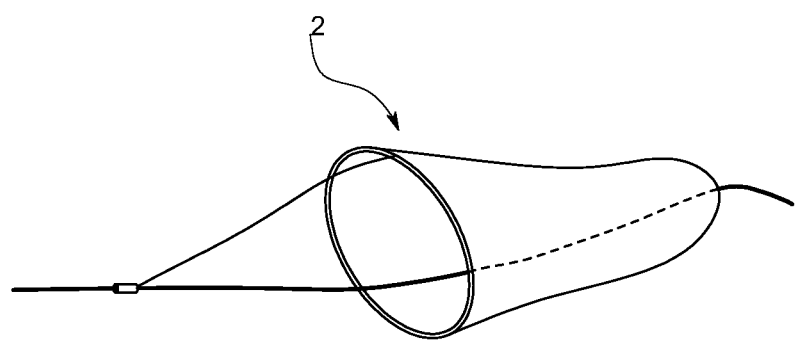
FIG. 31 is a schematic diagram illustrating a filter member in another embodiment of the present invention.

Note that the present invention is not limited to any of the above-described embodiments. For example, as the filter member, the present invention can also be applied to a filter member of a type as illustrated in FIG. 31.

Figure 32:
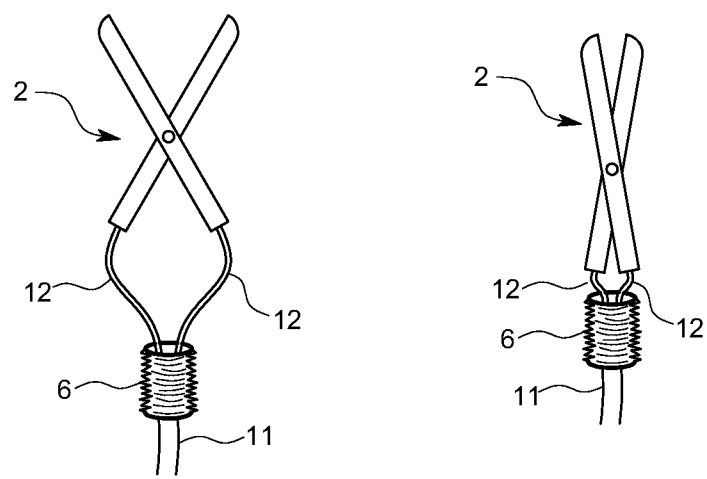
FIG. 32 is a schematic diagram illustrating a medical tool main body in still another embodiment of the present invention.

Further, the present invention can also be applied to a medical tool main body other than the filter member, such as a grasping forceps, scissors, or suture instrument used for endoscopic surgery at present, which can be minimized. For example, FIG. 32 illustrates a schematic diagram of scissors 2' as the medical tool main body. The outer tube 11 is attached with two forked elastic wires 12 as cores, and the tip parts of the elastic wires 12 are attached to the base end parts of respective blades of the scissors 2'. The scissors 2' are contained in the containing member 6 and conveyed, and after released out of the containing member 6, by operating the outer tube 11 to move the containing member 6 forward and backward, the scissors 2' can be driven. After the end of treatment, the containing member is pushed forward to bring the scissors into a closed state, and the scissors are directly withdrawn outside the body, or withdrawn in the containing member and then withdrawn outside the body. Note that the scissors are biased in the scissors opening direction by an unillustrated elastic body.

In addition, as a result of the minimization, the medical tool main body such as the grasping forceps, scissors, or suture instrument can be applied for intravascular treatment. The intravascular treatment is an area where future development is expected. The intravascular treatment sends a treatment tool in a vascular cavity to a target focus mainly under guide wire guidance to provide treatment. Accordingly, as in the present invention, in the case where the treatment tool itself have a function as a guide wire that guides another treatment tool, multiple treatment tools can be gathered near the one treatment tool, and consequently a complicated treatment operation can be performed.

Further, at present, it is impossible to use multiple treatment tools for one focus because in many cases, a vascular cavity of an access route to a focus is narrower than that of a focus area; however, according to the present invention, an advanced treatment tool can be made to reach a focus with an extra fine outer tube being left in an access route, and therefore even in the case where a vascular cavity of an access route is narrow, multiple treatment tools can be inserted to a focus area to provide complicated treatment as with endoscopic surgery.

Besides, the present invention may appropriately combine the respective embodiments described above or parts of the elements illustrated in the drawings.

REFERENCE CHARACTERS LIST

100: Medical tool (intravascular free piece capturing tool)
11: Outer tube
12: Core
2: Medical tool main body (filter member)
21: Filter
22: Elastic ring
3: Suspension lines
6: Containing member

The invention claimed is:
1. A medical tool comprising:
an outer tube that is inserted into a body;
a core that is inserted into the outer tube so as to be movable forward and backward;

a filter member that is attached to the core at a portion of the core protruding from the outer tube, and is operable by a predetermined driving force; and a tubular containing member with an open fore end that is positioned at a fore end of the outer tube and configured to contain the filter member in a folded state when the filter member is inserted into the body, wherein by moving the outer tube backward relative to the core, the medical tool is configured to release the filter member out of the containing member in a target site in the body in an unfolded state, and by moving the outer tube forward relative to the core, the containing member is configured to approach the released filter member in the target site in the body, thereby applying the driving force on the filter member that collapses the filter member into the folded state without the filter member entering the containing member.

2. The medical tool according to claim 1, wherein:

the containing member in a compressed and deformed state along the axis of the core, is configured to approach the filter member and apply the driving force on the filter member.

3. The medical tool according to claim 1, wherein:

an outer diameter of the outer tube is 0.012 inches, 0.014 inches, or 0.016 inches.

4. The medical tool according to claim 1, wherein:

the filter member has a bag like filter with an opening, and is adapted to capture a thrombus or other free piece entering inside from the opening, the filter member is contained in the containing member in the folded state when inserted into a blood vessel, and is placed in the unfolded state with its opening being open when released out of the containing member in the target site in the blood vessel, and by moving the outer tube forward relative to the core, the containing member is configured to approach the filter member, thereby applying the driving force that closes the opening of the filter member.

5. The medical tool according to claim 4, wherein:

the filter member further comprises an elastic ring that is attached to the opening of the filter member and enables the filter member to open the opening by an elastic restoring force, the filter member is attached to the core by multiple suspension lines that extend from multiple positions on the elastic ring to a single attachment point on the core, the medical tool further comprises a second tube that is wrapped around the core and is able to slide along the core, and which is located at an operating end side of the attachment point of the multiple suspension lines, by moving the outer tube forward relative to the core, the containing member is configured to approach the unfolded filter member, then compress and deform as it pushes the second tube, and as the second tube is pushed, it draws the multiple suspension lines into the second tube, thereby applying a contractile force on the elastic ring of the filter member to close the opening of the filter member as well as to bring the filter member into a folded state, at which the filter member is ready to be withdrawn.

6. The medical tool according to claim 5, wherein:

in the folded state, the elastic ring is configured to be folded alternately away from and towards an operating end of the medical tool, forming a total of four alternating mountain and valley folds, and forcing a portion of the elastic ring that is near to the operating end of the medical tool to bite on the second tube, and in this state, a combined substantial diameter of the second tube including the portion of the elastic ring that bites on it, is equal to or smaller than a substantial diameter of the compressed and deformed containing member.

7. The medical tool according to claim 4, wherein:

the filter member further comprises an elastic ring that is attached to the opening of the filter member and enables the filter member to open the opening by an elastic restoring force, the filter member is attached to the core by multiple suspension lines that extend from multiple positions on the elastic ring to a single attachment point on the core, by moving the outer tube forward relative to the core, the containing member is configured to approach the unfolded filter member, compress and deform as it comes into abutting contact with the multiple suspension lines, and as the containing member contacts with the multiple suspension lines, it draws the multiple suspension lines into the containing member, thereby applying a contractile force on the elastic ring of the filter member to close the opening of the filter member as well as to bring the filter member into a folded state, at which the filter member is ready to be withdrawn.

8. The medical tool according to claim 7 wherein:

in the folded state, the elastic ring is configured to be folded alternately away from and towards an operating end of the medical tool, forming a total of four alternating mountain and valley folds, and forcing the portion of the elastic ring that is near to the operating end of the medical tool to bite on a far side portion, relative to the operating end, of the compressed and deformed containing member, and in this state, a substantial radius of the far side portion, relative to the operating end, of the compressed and deformed containing member is smaller than the substantial radius of the near side portion, relative to the operating end, of the compressed and deformed containing member.

9. The medical tool according to claim 8, wherein:

the value obtained from subtracting the substantial radius of the near side portion of the compressed and deformed containing member, from the substantial radius of the far side portion of the compressed and deformed containing member, is set to be equal to or larger than the wire-diameter of the elastic ring.

10. A medical tool comprising:

an outer tube that is inserted into a body;

a core that is inserted into the outer tube so as to be movable forward and backward;

a medical tool main body that is attached to the core at a portion of the core protruding from the outer tube, and is operable by a predetermined driving force; and a tubular containing member with an open fore end that is positioned at a fore end of the outer tube and configured to contain the medical tool main body when the medical tool main body is inserted into the body, wherein by moving the outer tube backward relative to the core, the medical tool is configured to release the medical tool main body out of the containing member in a target site in the body, and by moving the outer tube forward relative to the core, the containing member in a compressed and deformed state in an axial direction along the axis of the core is configured to approach the released medical tool main body in the target site in the body, thereby applying the driving force on the medical tool main body.

11. A method for using a medical tool, the medical tool comprising:
- an outer tube;
- a core that is inserted into the outer tube so as to be movable forward and backward;
- a filter member that is attached to the core at a portion of the core protruding from the outer tube, and is operable by a predetermined driving force; and
- a tubular containing member with an open fore end that is positioned at a fore end of the outer tube and configured to contain the filter member in a folded state when the filter member is inserted into the body, the method comprising the steps of:
- inserting the medical tool into a body;
- moving the outer tube backward relative to the core, thereby releasing the filter member from the containing member at the target site in the body in an unfolded state; and
- moving the outer tube forward relative to the core, causing the containing member to approach the filter member in the target site, thereby applying the driving force to the filter member that collapses the filter member into the folded state without the filter member entering the containing member.

* * * * *